United States Patent
Hoffman et al.

(10) Patent No.: US 7,606,401 B2
(45) Date of Patent: Oct. 20, 2009

(54) SYSTEM AND METHOD FOR PROCESSING TOKENLESS BIOMETRIC ELECTRONIC TRANSMISSIONS USING AN ELECTRONIC RULE MODULE CLEARINGHOUSE

(75) Inventors: Ned Hoffman, Berkeley, CA (US); Philip Dean Lapsley, Oakland, CA (US)

(73) Assignee: YT Acquisition Corporation, Delray Beach, FL (US)

( * ) Notice: Subject to any disclaimer, the term of this patent is extended or adjusted under 35 U.S.C. 154(b) by 720 days.

(21) Appl. No.: 11/198,121

(22) Filed: Aug. 4, 2005

(65) Prior Publication Data
US 2005/0289058 A1  Dec. 29, 2005

Related U.S. Application Data

(63) Continuation of application No. 09/398,914, filed on Sep. 16, 1999, which is a continuation of application No. 09/244,784, filed on Feb. 5, 1999, now Pat. No. 6,012,039, which is a continuation of application No. 08/705,399, filed on Aug. 29, 1996, now Pat. No. 5,870,723, which is a continuation-in-part of application No. 08/442,895, filed on May 17, 1995, now Pat. No. 5,613,012, which is a continuation-in-part of application No. 08/345,523, filed on Nov. 28, 1994, now Pat. No. 5,615,277.

(51) Int. Cl.
*G06K 9/00* (2006.01)
(52) U.S. Cl. .................... 382/124; 382/126; 713/181
(58) Field of Classification Search ............. 382/124; 705/39
See application file for complete search history.

(56) References Cited

U.S. PATENT DOCUMENTS
3,639,905 A  2/1972  Yaida et al.
(Continued)

FOREIGN PATENT DOCUMENTS
EP  0581421 A1  2/1994
(Continued)

OTHER PUBLICATIONS
"Biometric ID Cards", story from Totse.com, Feb. 1996.
(Continued)

*Primary Examiner*—Evens J Augustin
(74) *Attorney, Agent, or Firm*—Marger Johnson & McCollom, P.C.

(57) ABSTRACT

Herein is described a tokenless biometric method for processing electronic transmissions, using at least one user biometric sample, an electronic identicator and an electronic rule module clearinghouse. The steps for processing of the electronic transmissions comprise of a user registration step, wherein a user registers with an electronic identicator at least one registration biometric sample taken directly from the person of the user. A formation of a rule module customized to the user in a rule module clearinghouse, wherein at least one pattern data of a user is associated with at least one execution command of the user. A user identification step, wherein the electronic identicator compares a bid biometric sample taken directly from the person of the user with at least one previously registered biometric sample for producing either a successful or failed identification of the user. In a command execution step, upon successful identification of the user, at least one previously designated rule module of the user is invoked to execute at least one electronic transmission. The above-mentioned steps are conducted in a manner wherein a biometrically authorized electronic transmission is conducted without the user presenting any personalized man-made memory tokens such as smartcards, or magnetic swipe cards.

103 Claims, 8 Drawing Sheets

U.S. PATENT DOCUMENTS

| | | |
|---|---|---|
| 3,876,864 A | 4/1975 | Clark et al. |
| 3,943,335 A | 3/1976 | Kinker et al. |
| 3,975,711 A | 8/1976 | McMahon |
| 4,048,618 A | 9/1977 | Hendry |
| 4,151,512 A | 4/1979 | Riganati et al. |
| 4,208,651 A | 6/1980 | McMahon |
| 4,213,038 A | 7/1980 | Silverman et al. |
| 4,227,805 A | 10/1980 | Schiller |
| 4,253,086 A | 2/1981 | Szwarcbier |
| 4,321,672 A | 3/1982 | Braun |
| 4,322,163 A | 3/1982 | Schiller |
| 4,353,056 A | 10/1982 | Tsikos |
| 4,358,677 A | 11/1982 | Ruell et al. |
| 4,390,968 A | 6/1983 | Hennessy |
| 4,429,413 A | 1/1984 | Edwards |
| 4,484,328 A | 11/1984 | Schlafly |
| 4,537,484 A | 8/1985 | Fowler et al. |
| 4,544,267 A | 10/1985 | Schiller |
| 4,582,985 A | 4/1986 | Lofberg |
| 4,618,988 A | 10/1986 | Schiller |
| 4,649,563 A | 3/1987 | Riskin |
| 4,675,815 A | 6/1987 | Kuroki |
| 4,696,046 A | 9/1987 | Schiller |
| 4,699,149 A | 10/1987 | Rice |
| 4,720,869 A | 1/1988 | Wadia |
| 4,728,186 A | 3/1988 | Eguchi et al. |
| 4,734,858 A | 3/1988 | Schlafly |
| 4,747,050 A | 5/1988 | Brachtl et al. |
| 4,752,966 A | 6/1988 | Schiller |
| D298,536 S | 11/1988 | Brefka |
| 4,784,484 A | 11/1988 | Jensen |
| 4,799,156 A | 1/1989 | Shavit et al. |
| 4,805,223 A | 2/1989 | Denyer |
| 4,821,118 A | 4/1989 | Lafreniere |
| 4,837,422 A | 6/1989 | Dethloff et al. |
| 4,845,636 A | 7/1989 | Walker |
| 4,868,376 A | 9/1989 | Lessin et al. |
| 4,926,480 A | 5/1990 | Chaum |
| 4,946,276 A | 8/1990 | Chilcott |
| 4,947,028 A | 8/1990 | Gorog |
| 4,947,443 A | 8/1990 | Costello |
| 4,961,142 A | 10/1990 | Elliott et al. |
| 4,993,068 A | 2/1991 | Piosenka et al. |
| 4,995,086 A | 2/1991 | Lilley et al. |
| 4,998,279 A | 3/1991 | Weiss |
| 5,025,372 A | 6/1991 | Burton |
| 5,036,461 A | 7/1991 | Elliott et al. |
| 5,054,089 A | 10/1991 | Uchida et al. |
| 5,054,090 A | 10/1991 | Knight et al. |
| 5,056,019 A * | 10/1991 | Schultz et al. ................. 705/14 |
| 5,073,950 A | 12/1991 | Colbert et al. |
| 5,077,803 A | 12/1991 | Kato et al. |
| 5,088,817 A | 2/1992 | Igaki et al. |
| 5,095,194 A | 3/1992 | Barbanell |
| 5,103,486 A | 4/1992 | Grippi |
| 5,105,467 A | 4/1992 | Kim et al. |
| 5,109,427 A | 4/1992 | Yang |
| 5,109,428 A | 4/1992 | Igaki et al. |
| 5,144,680 A | 9/1992 | Kobayashi |
| 5,145,102 A | 9/1992 | Minato et al. |
| 5,146,102 A | 9/1992 | Higuchi et al. |
| 5,161,204 A | 11/1992 | Hutcheson et al. |
| 5,168,520 A | 12/1992 | Weiss |
| 5,180,901 A | 1/1993 | Hiramatsu |
| 5,191,611 A | 3/1993 | Lang |
| 5,210,588 A | 5/1993 | Lee |
| 5,210,797 A | 5/1993 | Usui et al. |
| 5,222,152 A | 6/1993 | Fishbine et al. |
| 5,224,164 A | 6/1993 | Eisner |
| 5,224,173 A * | 6/1993 | Kuhns et al. ................. 382/116 |
| 5,229,764 A | 7/1993 | Matchett et al. |
| 5,230,025 A | 7/1993 | Fishbine |
| 5,239,583 A | 8/1993 | Parrillo |
| 5,241,606 A | 8/1993 | Horie |
| 5,251,259 A | 10/1993 | Mosley |
| D340,919 S | 11/1993 | Lee |
| 5,265,162 A | 11/1993 | Bush et al. |
| 5,267,324 A | 11/1993 | Kumagai |
| 5,274,695 A | 12/1993 | Green |
| 5,276,314 A | 1/1994 | Martino et al. |
| 5,280,527 A | 1/1994 | Gullman et al. |
| 5,280,627 A | 1/1994 | Flaherty et al. |
| 5,321,242 A | 6/1994 | Heath, Jr. |
| 5,321,765 A | 6/1994 | Costello |
| 5,325,442 A | 6/1994 | Knapp |
| 5,329,589 A | 7/1994 | Fraser et al. |
| 5,335,288 A | 8/1994 | Faulkner |
| 5,343,529 A | 8/1994 | Goldfine et al. |
| 5,351,303 A | 9/1994 | Willmore |
| 5,354,974 A | 10/1994 | Eisenberg |
| 5,359,669 A | 10/1994 | Shanley et al. |
| 5,371,794 A | 12/1994 | Diffie et al. |
| 5,371,797 A | 12/1994 | Bocinsky, Jr. |
| 5,383,113 A | 1/1995 | Kight et al. |
| 5,386,104 A | 1/1995 | Sime |
| 5,400,662 A | 3/1995 | Tamori |
| 5,412,738 A | 5/1995 | Brunelli et al. |
| 5,416,573 A | 5/1995 | Sartor, Jr. |
| 5,429,006 A | 7/1995 | Tamori |
| 5,457,747 A | 10/1995 | Drexler |
| 5,465,290 A | 11/1995 | Hampton et al. |
| 5,465,303 A | 11/1995 | Levison et al. |
| 5,466,919 A | 11/1995 | Hovakimian |
| 5,469,506 A | 11/1995 | Berson et al. |
| 5,484,988 A | 1/1996 | Hills et al. |
| 5,485,510 A | 1/1996 | Colbert |
| D367,044 S | 2/1996 | Arakaki |
| 5,493,621 A | 2/1996 | Matsumura |
| 5,499,288 A | 3/1996 | Hunt et al. |
| 5,513,272 A | 4/1996 | Bogosian, Jr. |
| 5,517,558 A | 5/1996 | Schalk |
| 5,533,123 A | 7/1996 | Force et al. |
| 5,534,855 A * | 7/1996 | Shockley et al. ............ 340/5.52 |
| 5,546,471 A * | 8/1996 | Merjanian ................... 382/124 |
| 5,546,523 A | 8/1996 | Gatto |
| 5,561,718 A | 10/1996 | Trew et al. |
| 5,572,597 A | 11/1996 | Chang et al. |
| 5,577,120 A | 11/1996 | Penzias |
| 5,598,474 A | 1/1997 | Johnson |
| 5,602,933 A | 2/1997 | Blackwell et al. |
| 5,604,802 A | 2/1997 | Holloway |
| 5,613,102 A | 3/1997 | Chiang et al. |
| 5,615,277 A | 3/1997 | Hoffman |
| 5,621,812 A | 4/1997 | Deaton et al. |
| 5,635,723 A | 6/1997 | Fujieda et al. |
| 5,636,038 A | 6/1997 | Lynt et al. |
| 5,636,282 A | 6/1997 | Holmquist |
| 5,647,364 A | 7/1997 | Schneider et al. |
| 5,650,217 A | 7/1997 | Skrivanek et al. |
| 5,655,116 A | 8/1997 | Kirk et al. |
| 5,677,989 A | 10/1997 | Rabin et al. |
| 5,719,950 A | 2/1998 | Osten et al. |
| 5,745,555 A | 4/1998 | Mark |
| 5,748,780 A | 5/1998 | Stolfo |
| 5,757,917 A | 5/1998 | Rose et al. |
| 5,764,789 A | 6/1998 | Pare, Jr. et al. |
| 5,768,134 A | 6/1998 | Swaelens et al. |
| 5,770,849 A | 6/1998 | Novis et al. |
| 5,787,187 A | 7/1998 | Bouchard et al. |
| 5,790,668 A | 8/1998 | Tomko |
| 5,794,207 A | 8/1998 | Walker et al. |
| 5,796,857 A | 8/1998 | Hara |
| D397,682 S | 9/1998 | Yotukura |
| 5,802,199 A | 9/1998 | Pare, Jr. et al. |

| | | |
|---|---|---|
| 5,805,719 A | 9/1998 | Pare, Jr. et al. |
| D400,191 S | 10/1998 | Butts et al. |
| 5,822,737 A | 10/1998 | Ogram |
| 5,825,907 A | 10/1998 | Russo |
| 5,825,924 A | 10/1998 | Kobayashi |
| 5,826,241 A | 10/1998 | Stein et al. |
| 5,826,245 A | 10/1998 | Sandberg-Diment |
| 5,832,464 A | 11/1998 | Houvener et al. |
| 5,838,812 A | 11/1998 | Pare, Jr. et al. |
| 5,844,287 A | 12/1998 | Hassan et al. |
| 5,845,005 A | 12/1998 | Setlak et al. |
| 5,848,400 A | 12/1998 | Chang |
| 5,850,442 A | 12/1998 | Muftic |
| 5,870,723 A | 2/1999 | Pare, Jr. et al. |
| 5,876,926 A | 3/1999 | Beecham |
| 5,892,824 A | 4/1999 | Beatson et al. |
| 5,892,838 A | 4/1999 | Brady |
| 5,910,988 A | 6/1999 | Ballard |
| 5,926,555 A | 7/1999 | Ort et al. |
| 5,930,804 A | 7/1999 | Yu et al. |
| 5,933,515 A | 8/1999 | Pu |
| 5,935,071 A | 8/1999 | Schneider et al. |
| 5,943,235 A | 8/1999 | Earl et al. |
| 5,943,423 A | 8/1999 | Muftic |
| 5,956,700 A | 9/1999 | Landry |
| 5,982,914 A | 11/1999 | Lee et al. |
| 5,986,746 A | 11/1999 | Metz et al. |
| 5,991,372 A | 11/1999 | Davenport D'Ingianni et al. |
| 6,011,858 A | 1/2000 | Stock et al. |
| 6,012,039 A | 1/2000 | Hoffman et al. |
| 6,016,476 A | 1/2000 | Maes et al. |
| 6,023,688 A | 2/2000 | Ramachandran et al. |
| 6,023,783 A | 2/2000 | Divsalar et al. |
| 6,028,950 A | 2/2000 | Merjanian |
| 6,029,195 A | 2/2000 | Herz |
| 6,040,783 A | 3/2000 | Houvener et al. |
| 6,041,309 A | 3/2000 | Laor |
| 6,045,039 A * | 4/2000 | Stinson et al. ............... 235/379 |
| 6,052,675 A | 4/2000 | Checchio |
| 6,064,751 A | 5/2000 | Smithies et al. |
| 6,070,141 A | 5/2000 | Houvener et al. |
| 6,072,894 A | 6/2000 | Payne |
| 6,073,840 A | 6/2000 | Marion |
| 6,084,967 A | 7/2000 | Kennedy et al. |
| 6,105,010 A | 8/2000 | Musgrave |
| 6,111,977 A | 8/2000 | Scott et al. |
| 6,119,096 A | 9/2000 | Mann et al. |
| 6,154,727 A | 11/2000 | Karp et al. |
| 6,154,879 A | 11/2000 | Pare, Jr. et al. |
| 6,182,076 B1 * | 1/2001 | Yu et al. ...................... 707/10 |
| 6,192,142 B1 | 2/2001 | Pare, Jr. et al. |
| 6,202,151 B1 | 3/2001 | Musgrave et al. |
| 6,208,746 B1 | 3/2001 | Musgrave |
| 6,219,439 B1 | 4/2001 | Burger |
| 6,230,148 B1 | 5/2001 | Pare, Jr. et al. |
| 6,233,565 B1 | 5/2001 | Lewis et al. |
| 6,233,618 B1 | 5/2001 | Shannon |
| 6,256,737 B1 | 7/2001 | Bianco et al. |
| 6,260,024 B1 | 7/2001 | Shkedy |
| 6,268,788 B1 | 7/2001 | Gray |
| 6,269,348 B1 | 7/2001 | Pare, Jr. et al. |
| 6,275,944 B1 | 8/2001 | Kao et al. |
| 6,310,966 B1 | 10/2001 | Dulude et al. |
| 6,311,272 B1 * | 10/2001 | Gressel ....................... 713/186 |
| 6,327,578 B1 | 12/2001 | Linehan |
| 6,366,682 B1 | 4/2002 | Hoffman et al. |
| 6,377,228 B1 | 4/2002 | Jenkin et al. |
| 6,397,198 B1 | 5/2002 | Hoffman et al. |
| 6,411,728 B1 | 6/2002 | Lee et al. |
| 6,522,772 B1 | 2/2003 | Morrison et al. |
| 7,133,792 B2 | 11/2006 | Murakami et al. |
| 7,152,787 B2 | 12/2006 | Cheng |
| 2001/0000045 A1 | 3/2001 | Yu et al. |
| 2001/0000535 A1 | 4/2001 | Lapsley et al. |
| 2001/0011247 A1 | 8/2001 | O'Flaherty et al. |
| 2001/0033661 A1 | 10/2001 | Prokoski |
| 2001/0034837 A1 | 10/2001 | Kausik et al. |
| 2001/0044775 A1 | 11/2001 | Saito et al. |
| 2003/0061172 A1 | 3/2003 | Robinson |

FOREIGN PATENT DOCUMENTS

| | | |
|---|---|---|
| EP | 0598469 A2 | 5/1994 |
| EP | 0 651 357 A1 | 5/1995 |
| EP | 0823701 A2 | 2/1998 |
| EP | 0652 540 B1 | 9/2000 |
| JP | S57-212851 | 12/1982 |
| JP | S59-36860 | 2/1984 |
| JP | 61-187838 | 8/1986 |
| JP | S63-003369 | 1/1988 |
| JP | 63-120385 | 5/1988 |
| JP | 63-261492 | 10/1988 |
| JP | 03-189756 | 8/1991 |
| JP | 03-288954 | 12/1991 |
| JP | 04-322382 | 11/1992 |
| JP | 04-324583 | 11/1992 |
| JP | 05-62057 | 3/1993 |
| JP | 05-250524 | 9/1993 |
| JP | 06-149980 | 5/1994 |
| JP | 06-176135 | 6/1994 |
| WO | WO94/10659 | 5/1994 |
| WO | WO95/13591 | 5/1995 |
| WO | WO98/25227 | 6/1997 |
| WO | WO98/09227 | 3/1998 |
| WO | WO98/50875 | 11/1998 |
| WO | WO99/28847 | 6/1999 |

OTHER PUBLICATIONS

"Biometric payment firm Pay By touch secures $10 million funding", story from Finextra.com, Oct. 2003.

"Biometrics Comparison Chart", ncsc.dni.us, 2002.

"Is it Time for Biometrics?", Banking Automation Bulletin for Europe, London, Sep. 1992, Issue 115, p. 1 (ProQuest document ID 7415352).

"Pay By Touch announces first UK Customer", May 2004.

"Supermarkets and Shopper Registration Guide", from Nocards.org., downloaded, Dec. 26, 2007.

"TCP Protocol Overview" downloaded Dec. 26, 2007.

"Why do you call them 'registration and monitoring' programs?", question from CASPIAN, Nocards.org., 2005.

Anderson, T.; "Security Management"; American Society for Industrial Security, v. 37, No. 11, Nov. 1993; pp. 17-19.

Cavoukian, Ann, "Consumer Biometric Applications: A Discussion Paper", Information and Privacy Commissioner, Ontario, Canada. Sep. 1999.

Cavoukian, Ann, Ph. D., "Building in Privacy", May 14-16, 1996. http://www.cpsr.org/cpsr/lists/rre/building_in_privacy. Online 2004.

Rechtin, Mark, "Fingerprint Technology Makes for Best ID System," Orange County Business Journal, Newport Beach, May 14, 1992, vol. 12, Issue 51, Sec. 1, p. 7 (Proquest document ID 6020297).

State of Virginia, Department of Social Services, "What are food stamps?" http://www.dss.virginia.gov/benefit/foodstamp.html, downloaded Nov. 10, 2005.

Holmes, et al., "A Performance Evaluation of Biometric Identification Devices"; Sandia National Laboratories; Albuquerque, NM; Jun. 1991.

Anderson, T., "Security Management"; v. 37, No. 11; Nov. 1993; pp.17-19.

Lange, et al.; "Digital Identification: It's Now at our Fingertips"; Electronic Engineering Times; No. 946; Mar. 24, 1997; p. 142.

Radcliff; "When Data Warehouse Become Open House"; Software Management; v. 16, No. 11; Nov. 26, 1996.

Anonymous; A Credit Union Points a Finger at Biometrics; Bank Network News; v. 15, No. 16; Jan. 13, 1997.

Hall, J; "Scanning Lets Fingerprints Do Talking"; *Toronto Star;* PA6, May 15, 1997.

Scally, R.; "CompUSA Tests Fingerprints to Help Secure Transactions"; *Discount Store News;* v. 36, No. 10, May 19, 1997.

Stosz, et al. "Automated System for Fingerprint Authentication Using Pores and Ridge Structure"; *Proceedings of The International Society for Optical Engineering;* v. 2277; Jul. 28-29, 1994; pp. 210-223.

Recently Granted Patents in the USA—Sep. 1998; Transponder News; (5 pages).

Toll, Janie, "Veridicom Showcases New Customers and Applications at COMDEX"; Press Release; Nov. 16, 1998; 3 pages.

Kolor, Joanna; "Biometric Technology Goes Live" *Bank Network News;* May 1, 1996; 7 pages.

\* cited by examiner

SYSTEM AND METHOD FOR PROCESSING TOKENLESS BIOMETRIC ELECTRONIC TRANSMISSIONS USING AN ELECTRONIC RULE MODULE CLEARINGHOUSE

CROSS REFERENCE

This application is a continuation of U.S. application Ser. No. 09/398,914 filed Sep. 16, 1999, now pending, which is a continuation of U.S. application Ser. No. 09/244,784 filed Feb. 5, 1999, now U.S. Pat. No. 6,012,039, which is a continuation of U.S. application Ser. No. 08/705,399, filed on Aug. 29, 1996 now U.S. Pat. No. 5,870,723, which is a continuation-in-part of U.S. application Ser. No. 08/442,895 filed on May 17, 1995 now U.S. Pat. No. 5,613,012 which is a continuation-in-part of U.S. application Ser. No. 08/345,523, filed on Nov. 28, 1994, now U.S. Pat. No. 5,615,277.

FIELD OF THE INVENTION

The invention relates generally to computer systems designed to execute electronic transmissions on behalf of users. More specifically, this invention relates to tokenless biometric computer systems which do not require the user to possess any man-made memory devices resident with user-customized information, such as smart cards, magnetic swipe cards or personal computers. This invention does not relate to any automated door lock or automated physical site access mechanisms.

BACKGROUND OF THE INVENTION

The use of electronic transmissions has proliferated with the advent of personal computers, or "terminals", and improved communications networks such as the Internet. Billions of electronic transmissions are sent and received each year in the United States. An electronic transmission, as used herein, is defined as the accessing, processing, or presentation of electronic data, to include word-processed content, mathematical spreadsheets, emails, visual or graphic images, audible content, software code, pattern data, execution commands, computer software programs, Internet web sites, software rule modules, electronic instant messaging, and the like. Such electronic transmissions may take many forms, including: an electronic request for user-customized or user-unique access to stored database content; an electronic request to customize the processing of data according to user-customized or user-unique criteria; and an electronic request to present or display data in a pre-determined, user-customized format.

It should be noted that user-customized is different from user-unique. Electronic data or electronic transmissions which are customized to a user, or "user-customized", have been customized by or for a user, but may not necessarily be unique to that user. Therefore, user-customized data which applies to one user may also apply similarly or identically to another user. However, electronic data or electronic transmissions which are unique to a user, or "user-unique", are distinctive and without equal, and hence are exclusive to that particular user.

In sum, an electronic transmission is the accessing, processing, or presentation of any electronic data or content which does not in and of itself constitute or execute either: an electronic financial transaction wherein the exchange or alteration of any financial assets occurs, nor; an automated door lock or an automated physical site access mechanism.

A result of the significant popularity of electronic transmissions has been a marketplace transition from using an off-line, individual desktop personal computing model to using an on-line, central-server communications model. Specifically, corporations and individual consumers are moving the main functions of storage, access, processing and presentation of their electronic transmissions from decentralized, unconnected desktop terminals, to centralized databases on servers which service and connect to on-line PCs, known as "client terminals", via dial-up, leased lines or wireless networks. In this transition, such client terminals are also increasingly being connected to each other. An integrated web of communications is forming that enormously expands the functions and benefits of using such clients, evidenced by fast growth of the Internet and corporate intranets.

At the same time, cost reductions in miniaturizing computer hardware components have led to the widespread use of a new generation of computing devices, known herein as "thin-clients", which are even less expensive and more mobile than traditional desktop terminals and client terminals. The appeal of these new thin-clients is that they offer the potential for the user to send and receive electronic transmissions at virtually any time and from virtually anywhere. Many of these lower cost thin-clients access much of their processing and memory capacities on-line from remote servers via Internet, intranet or extranet connections. These thin-client devices include, but are not limited to: wireless pagers; wireless and tethered telephones; network computers; thin-client exercise machines; electronic books; public access kiosks such as automated teller machines, vending machines, airport information terminals and or public kiosks; hand-held personal digital assistants such as Palm Pilots™ and the like; on-line photocopy machines; automobile embedded Internet-connected appliances which download preferred radio stations, seat and temperature adjustments, and the like; thin-client household appliances such as refrigerators, microwaves, and the like; thin-client home entertainment appliances including on-line televisions such as WebTV™, portable digital audio systems such as the Rio™, along with their associated remote controls.

These two trends, of proliferating personal computing devices and of increased on-line communications usage, have led to a distinct problem: with so may personal computing devices, the user now has user-customized electronic data stored on multiple man-made memory devices, or "tokens", which the user must manage and possess for storage, access, processing and presentation of their electronic transmissions. Further, if the user wants all of these new computing tokens to possess the same capabilities with respect to the user's personalized information and customized functions, then the user needs to frequently and redundantly enter all such user-customized data into each token. This is a cumbersome burden which most consumers eschew. If, on the other hand, the user does not effect such redundancies, then losing or damaging their primary personal computing token would be a severe blow. In this instance, or even in the instance where the user loses or damages a computing token with a subset of their information, then months, and perhaps years, of important personal and likely confidential electronic transmissions could be irretrievably lost, or revealed to an untrusted third-party.

In sum, the multitude of such personal computing tokens, whether unconnected desktop terminals or on-line hand held thin clients, has exacerbated the problem of user-reliance on particularly vulnerable, customized memory tokens which can be easily damaged, lost or stolen.

To protect these tokens and the resident electronic transmissions they contain, the use of various biometrics, such as fingerprints, hand prints, voice prints, retinal images, handwriting samples and the like have been suggested for identification of individuals. However, because the biometrics are generally themselves stored in electronic, and thus reproducible, form on the token itself and because the comparison and verification process is not isolated from the hardware and software directly used by the user attempting access, the problems of fraudulent access and of having to constantly carry these tokens is not alleviated. Further, such systems do not adequately isolate the identity verification process from tampering by someone attempting to gain unauthorized access. Examples of this approach to system security are described in U.S. Pat. No. 4,821,118 to Lafreniere; U.S. Pat. No. 4,993,068 to Piosenka et al.; U.S. Pat. No. 4,995,086 to Lilley et al.; U.S. Pat. No. 5,054,089 to Uchida et al.; U.S. Pat. No. 5,095,194 to Barbanell; U.S. Pat. No. 5,109,427 to Yang; U.S. Pat. No. 5,109,428 to Igaki et al.; U.S. Pat. No. 5,144,680 to Kobayashi et al.; U.S. Pat. No. 5,146,102 to Higuchi et al.; U.S. Pat. No. 5,180,901 to Hiramatsu; U.S. Pat. No. 5,210,588 to Lee; U.S. Pat. No. 5,210,797 to Usui et al.; U.S. Pat. No. 5,222,152 to Fishbine et al.; U.S. Pat. No. 5,230,025 to Fishbine et al.; U.S. Pat. No. 5,241,606 to Horie; U.S. Pat. No. 5,265,162 to Bush et al.; U.S. Pat. No. 5,321,242 to Heath, Jr.; U.S. Pat. No. 5,325,442 to Knapp; U.S. Pat. No. 5,351,303 to Willmore, all of which are incorporated herein by reference.

An example of a token-based security system which relies on a biometric of a user can be found in U.S. Pat. No. 5,280,527 to Gullman et al. In Gullman's system, the user must carry and present a credit card sized token (referred to as a biometrics security apparatus) containing a microchip in which is recorded characteristics of the authorized user's voice. In order to initiate the access procedure, the user must insert the token into a terminal such as a public kiosk, and then speak into the terminal to provide a biometrics input for comparison with an authenticated input stored in the microchip of the presented token. The process of identity verification is generally not isolated from potential tampering by one attempting unauthorized access. If a match is found, the remote terminal may then signal the host computer that access should be permitted, or may prompt the user for an additional code, such as a PIN (also stored on the token), before sending the necessary verification signal to the host computer.

Although Gullman's reliance of comparison of stored and input biometrics potentially reduces the risk of unauthorized access as compared to numeric codes, like personal identification numbers, Gullman's use of the token as the repository for the authenticating data combined with Gullman's failure to isolate the identity verification process from the possibility of tampering greatly diminishes any improvement to fraud resistance resulting from the replacement of a numeric code with a biometrics. Further, the system remains cumbersome and inconvenient to use because it too requires the presentation of a personalized memory token in order to initiate an access request.

Almost uniformly, prior art disclosing biometrics are token-based systems which teach away from biometrics recognition without user-dependence on personalized memory tokens. Reasons cited for such teachings range from storage requirements for biometrics recognition systems to significant time lapses in identification of a large number of individuals, even for the most powerful computers.

In view of the foregoing, there has long been a need for a computerized electronic transmissions system which enables the user to universally access, process and present their electronic transmissions with optimal convenience by not requiring the user to possess any man-made memory tokens on which must be stored the user's customized in order for the user to execute electronic transmissions. Further, there is a need for a tokenless computer system which is highly fraud-resistant, and which is centered around the individual themselves by relying solely upon their unique biometric samples. Such a system should be able to function for the user wherever and whenever the user may be using any generic on-line computing device, whether a desktop or a thin client, for conducting their electronic transmissions.

Further, there is a need for a computing system that provides the user with centralized storage, access, processing and presentation of their electronic transmissions regardless of whether the personal computing device the user is using possesses only a resident subset of their user-customized data or in fact possesses none of their user-customized data at all. Further, there is a need for a computerized electronic transmissions system that provides the user with the above benefits whether or not the personal computing device the user may be using at any given time contains powerful resident memory and processing capacities, or whether it contains virtually no resident memory and processing capacities. Further, there is a need for a computer system which relieves the user from having to redundantly data-enter and update a variety of individual personal computing devices in order to achieve the same customized performance from any or all of such devices.

There is also a need for a computerized electronic transmissions system which relieves the user from having to redundantly data-enter their personal demographics, age, and customized Internet usage activity information into a variety of Internet web sites in order to achieve uniformly customized service at each such web sites. Additionally, there is a need for a computerized electronic transmissions system which enables a user to benefit from executing customized and complex commands governing their electronic transmissions regardless of whether the on-line computing device the user happens to be using is a high-powered desktop terminal or whether it is a hand-held, ultra thin-client terminal with virtually no resident computer processing or memory capabilities of its own.

There is also a need for an electronic transmissions system that uses a strong link to the person being identified, as opposed to merely verifying a user's possession of any physical objects that can be freely transferred.

There is a further need for an electronic transmissions system that ensures user convenience by enabling user-authorization without requiring the user to possess, carry, and present one or more proprietary memory tokens, such as man-made user-customized portable memory devices, in order to effect electronic transmissions. Anyone who has lost a smart card or a traditional notebook personal computer, left it at home, had it damaged or stolen knows well the keenly and immediately-felt inconvenience caused by such problems. Therefore, there is a need for an electronic biometric transmissions system that is entirely tokenless.

There is another need in the industry for a computerized electronic transmissions system that is sufficiently versatile to accommodate both users who desire to use personal identification codes (PICs), being alphabetical, numerical or graphical, for added security and also consumers who prefer not to use them.

Lastly, such a system must be affordable and flexible enough to be operatively compatible with existing networks having a variety of electronic transmission devices and system configurations.

OBJECTIVES OF THE INVENTION

It is an objective of the invention to provide a computerized electronic transmissions system and method that eliminates the need for a user to directly possess any man-made memory token which is encoded or programmed with data personal to or customized for a single authorized user, such as a smart card, magnetic swipe card or even a personal computer with resident user-customized data. Further, it is an objective of the invention to employ a user's biometric sample for ensuring that only authorized users can access and conduct on their own electronic transmissions. It is another object of the invention to be a tokenless technology for ensuring that users have the portability and mobility to gain immediate access to their electronic transmissions via any network-connected interface, regardless of the resident capabilities of the computing device the user is using to interface with the computer network and a central server.

In another objective of the invention, the user's biometric records are used together with the user's age. The user's registration biometric sample may be sent to a database which stores the various users' biometric records. The user's registration biometric sample contains a reference of the user's age. At the database, the user's biometric sample is compared to the biometric record stored in the database. The system then determines whether the user's biometric sample matches the biometric record stored in the database or databases. If the user's biometric sample matches the biometric record stored in the database, then a second determination is made as to whether the user's age information in the reference meets the system parameter. It is a further objective of the system that a user's age is mapped to the biometric record and if it meets the system parameter, then the system approves the age-restricted transaction and the transaction is approved by showing a confirmation message to the user.

It is another object of this invention, that any client terminal, such as a public computing kiosk without resident user-customized data and without extensive resident software, be automatically and nearly instantly transformed, via a user's biometric log-on using this invention, into a terminal receiving on-line sophisticated computing capabilities that are customized for the user, complete with user-customized electronic transmission accessing, processing and presentation. It is further an object of this invention that the user be able to receive customized presentation of: their own Internet web portal displaying all URLs with which the user has pre-registered for access privileges; personalized recommendations for local activities, events and people that reflect their priorities; their Internet web site preferences, or "bookmarks"; and their Internet "cookies", or that set of data that an Internet website server provides to a user each time the user visits the website. It is further an object of this invention, that a central database save the information the cookies contains about the user, as a text file stored in the Netscape or Explorer system folder, and that this data can be temporarily downloaded this data to whatever client terminal the user is currently logged onto.

It is another object of this invention to provide a computerized electronic transmissions system centered around the user rather than any devices he may possess. In particular, this invention provides an electronic transmission system that is universally accessible to the user because he only needs his biometric to log onto a network, rather than having to rely on his having to possess any man-made memory tokens. In a traditional "unit-centric" communications model, the unit is any personalized memory token on which is stored user-customized electronic data, or information, that is: a) customized and perhaps even unique to a single user, and; b) required to execute an electronic transmission based on electronic data customized to a particular user's specifications or preferences. As such, the use or presentation of that memory token is a requirement for the user to conduct electronic transmissions which contains content customized, if not unique, to the user's criteria.

In this invention, emphasizing a "user-centric" communications model, there is no need for any memory token to be required by the user to execute an electronic transmission. This invention employs a user's biometric identification to enable a user to centrally store, access, process and present any customized electronic transmission independent of which computing device the user is using, whether it be a generic public kiosk with no resident information personalized to the user, or a hand held thin client with a minimal subset of data personalized to the user. In this invention, the computing and memory capabilities resident within the user's personal computing device are nearly irrelevant, so long as the device can connect to an on-line network, such as the Internet, and provides the user with basic biometric input, data input and data display means.

Yet another object of this invention is to construct and present for the user, on any biometric input apparatus the user may be using, a user-customized gateway to the Internet containing their desired bookmarks, their personalized search engine and their customized web page directory. This is the user's personal Internet web page "portal" which is a starting point for their electronic transmissions, including electronic mail, Internet web browsing or "surfing", and the like.

A further object of this invention is that in all of these electronic transmissions, this invention provides the user the ability, with only a biometric log-on, to automatically enter all restricted or confidential third-party databases throughout the Internet to which the user has pre-authorized access privileges.

It is another object of this invention that once the user has completed their Internet usage of the client terminal for a particular on-line session, all of the data stream from their on-line session, including all new cookies provided by third parties on behalf of the user and all new data on their browsing activity, be batched and forwarded to central database for downloading and storage.

It is another object of the invention to provide a computer system that is capable of verifying a user's identity, as opposed to verifying possession of propriety objects and information. It is yet another object of the invention to verify user identity based on one or more unique biometric characteristics physically personal to the user. Yet another object of the invention is to provide a computer system wherein access is secure, yet designed to be convenient and easy for a consumer to use.

It is yet another object of the invention to further enhance fraud resistance by maintaining authenticating data and carrying out the identity verification operations at a point in the system that is operationally isolated from the user requesting access, thereby preventing the user from acquiring copies of the authenticating data or from tampering with the verification process.

Yet another object of the invention is to provide a user with a central computerized data processing center, containing an electronic identicator and an electronic clearinghouse, for storage, accessing, processing and presenting their biometric and their user-customized electronic transmissions. As such, it is an objective of the invention to enable a user to enter their customized data into a centralized database, such data to include their biometric samples, their demographics, their computer function preferences, and their on-line activity or browsing patterns, and to thereby enable the user to have all such personal data uniformly updated by him and uniformly accessible to him regardless of the computing device the user is using at any one time.

Yet another object of the invention is to enable third-party databases to correctly identify a user using the computer system so that their on-line activity patterns can be linked to that user's personal demographic database. In this way, the third-party can more efficiently deliver services and information to pre-identified or interested users.

Another objective of the invention is that the third-party database be identified by the computer system, wherein the third-party database's identification is verified.

Another objective of the invention is to be added in a simple and cost-effective manner to existing computing terminals currently installed at points of usage and used over the Internet. Yet another objective of the invention is to be efficiently and effectively operative with existing communications systems and protocols, specifically as these systems and protocols linked to the processing of electronic transmissions.

SUMMARY OF THE INVENTION

Herein is described a tokenless biometric method for processing electronic transmissions, using at least one user biometric sample, an electronic identicator and an electronic rule module clearinghouse. The steps for processing of the electronic transmissions comprise of a user registration step, wherein a user registers with an electronic identicator at least one registration biometric sample taken directly from the person of the user. A formation of a rule module customized to the user in a rule module clearinghouse, wherein at least one pattern data of a user is associated with at least one execution command of the user. A user identification step, wherein the electronic identicator compares a bid biometric sample taken directly from the person of the user with at least one previously registered biometric sample for producing either a successful or failed identification of the user. In a command execution step, upon successful identification of the user, at least one previously designated rule module of the user is invoked to execute at least one electronic transmission. The above-mentioned steps are conducted in a manner wherein a biometrically authorized electronic transmission is conducted without the user presenting any personalized manmade memory tokens such as smartcards, or magnetic swipe cards.

Preferably during the command execution step, the electronic rule module clearinghouse communicates with one or more third-party computers, the third party computers having execution modules that can access, process, or display database contents.

Execution commands are comprised of any of the following, accessing stored electronic data customized to the user's rule modules, processing electronic data customized to the user's rule modules, and presentation of electronic data customized to the user's rule modules.

Pattern data comprises of any of the following; a user unique identification code, demographic information, an email address, a financial account, a secondary biometric, internet browsing patterns, a non-financial data repository account, a telephone number, a mailing address, purchasing patterns, data on pre-paid accounts or memberships for products or services, electronic data usage patterns, employee status, job title, data on user behavior patterns, a digital certificate, a network credential, an internet protocol address, a digital signature, an encryption key, an instant messaging address, personal medical records, an electronic audio signature, and an electronic visual signature.

The pattern data for a user is provided for the rule module by any of the following entities, the user, the electronic rule module clearinghouse, or an authorized third party.

The execution command for a user is provided for the rule module by any of the following; the user, the electronic rule module clearinghouse, or an authorized third party.

Preferably a user re-registration check step is used, wherein the user's registration biometric sample is compared against previously registered biometric samples wherein if a match occurs, the computer system is alerted to the fact that the user has attempted to reregister with the electronic identicator.

It is understood that the biometric sample comprises any of the following: a fingerprint, a facial scan, a retinal image, an iris scan, and a voice print.

In a different embodiment of the invention, during the identification step, the user provides a personal identification code to the electronic identicator along with a bid biometric sample for purposes of identifying the user.

In yet another embodiment, a biometric theft resolution step is employed, wherein a user's personal identification code is changed when the user's biometric sample is determined to have been fraudulently duplicated.

In a different embodiment, there is a convenient and secure way to conduct an age verification in an age-restricted transaction with the use of a biometric read (such as a fingerprint) and without the use of any age-verifying token.

In another embodiment, a system and method deter individuals from presenting fraudulent identification during an age-verification transaction at an unattended device.

In another embodiment, a system allows an individual to present age verifying and then to use a biometric sample to verify their age and verify their identity thereafter at participating devices in the system.

In a different embodiment, accessing stored electronic data results in activation of an internet-connected device, such as an exercise device that is connected to the Internet.

In a different embodiment, processing comprising of data includes invoking any of the following; a user's digital certificate, a user's identity scrambler, a user's interactive electronic consumer loyalty or consumer rewards program, a user's interactive electronic advertising, a user's interactive instant messaging program, a user's email authentication, and an automated electronic intelligent agent for electronic data search and retrieval that is customized to the user's requests.

Preferably, the invention comprises a user log-in repeat step, wherein during an electronic transmission the user is periodically required by the electronic identicator to present the user's bid biometric sample or at least one of the user's pattern data.

In another embodiment the method comprises a third-party registration step, wherein a third-party registers identification data with the electronic identicator, the identification data comprising any of the following; a biometric, a digital certificate, an internet protocol address, or a biometric input apparatus hardware identification code. In a third-party identification step, a third-party providing the user with electronic transmissions is identified by the electronic identicator by comparing the third-party's bid identification data with the third-party's registered identification data.

A computer system device for tokenless biometric processing of electronic transmissions, using at least one user biometric sample, an electronic identicator and an electronic rule module clearinghouse, comprises a biometric input apparatus, for providing a bid or registration biometric sample of a user to the electronic identicator; wherein a user registers with an electronic identicator at least one registration biometric sample taken directly from the person of the user; an electronic rule module clearinghouse, having at least one rule module further comprising at least one pattern data of the user associated with at least one execution command of the user, for executing at least one electronic transmission; an electronic identicator, for comparing the bid biometric sample with registered biometric samples of users; a command execution module, for invoking at least one previously designated execution command in the electronic rule module clearinghouse to execute an electronic transmission; wherein no man-made memory tokens such as smartcards, or magnetic swipe cards are presented by the user to conduct the electronic transmission.

Preferably the command execution module communicates with one or more third-party computers. Pattern data forte device of this invention comprises any of the following; a user unique identification code, demographic information, an email address, a financial account, a secondary biometric, a non-financial data repository account, a telephone number, a mailing address, purchasing patterns, data on pre-paid accounts or memberships for products or services, electronic data usage patterns, employee status, job title, data on user behavior patterns, a digital certificate, a network credential, an internet protocol address, a digital signature, an encryption key, an instant messaging address, personal medical records, the user's age information, an electronic audio signature, and an electronic visual signature. The pattern data for a user is provided for the rule module by any of the following; the user, the electronic rule module clearinghouse, or an authorized third party.

An execution command for a user is provided for the rule module by any of the following; the user, the electronic rule module clearinghouse, or an authorized third party.

In another embodiment of the invention a tokenless biometric method for processing electronic transmissions, using at least one user biometric sample, an electronic identicator and an electronic rule module clearinghouse, said method comprising the steps of a primary and subordinated user registration step, wherein a primary and subordinated user each register with an electronic identicator at least one registration biometric sample taken directly from the person of the primary and subordinated user, respectively. A rule module customized to the primary and subordinated user is formed in a rule module clearinghouse, wherein at least one pattern data of the primary and subordinated user is associated with at least one execution command of the primary and subordinated user. In a subordinated user identification step, the electronic identicator compares a bid biometric sample taken directly from the person of the subordinated user with at least one previously registered biometric sample for producing either a successful or failed identification of the subordinated user. In a subordination step, upon successful identification of the subordinated user, the pattern data of the subordinated user is searched to determine if any of the subordinated user's rule modules is subordinated to at least one of the primary user's rule modules. In a command execution step, upon the successful identification of the subordinated user, the subordinated user's age, and the determination that at least one of the subordinated user's rule modules is subordinated to at least one of the primary user's rule modules, at least one previously designated execution command of the primary user is invoked to execute at least one electronic transmission; wherein a biometrically authorized electronic transmission is conducted without the primary and subordinated user presenting any personalized man-made memory tokens such as smartcards, or magnetic swipe cards.

The present invention satisfies several needs by providing a significantly improved system and method for tokenless accessing, processing and presentation of electronic transmissions requiring only a user biometric.

The present invention is significantly advantageous over the prior art in a number of ways. First, it is extremely easy and efficient for people to use because it eliminates the need for users to directly possess any personalized memory tokens such as magnetic swipe cards or personal computers with resident user-customized data, in order to access, process and present electronic transmissions. The present invention therefore eliminates the inconveniences associated with carrying, safeguarding, and locating such memory laden tokens. The user is now uniquely empowered, by means of this invention, to conveniently conduct their electronic transmissions at any time and from virtually anywhere without dependence upon any tokens which may be stolen, lost or damaged.

The invention is clearly advantageous from a convenience standpoint by making electronic transmissions less cumbersome and more spontaneous.

Further, the substantial manufacturing and distributing costs of issuing and reissuing user-customized tokens such as magnetic swipe cards, and smart cards, or even powerful desktop personal computers, thereby providing further economic savings to users and companies.

Further, the present invention even eliminates the traditional requirement for a user to directly possess and use the ultimate memory token, a desktop personal computer with resident user-customized data.

Further, the present invention is also clearly advantageous from a convenience standpoint of users by providing centralized database tracking and storage of user-customized demographics, age, preferences and on-line activity or browsing patterns, thereby making electronic transmissions significantly more accurately and more precisely user-customized.

Moreover, the invention is markedly advantageous and superior to existing systems in being highly fraud resistant. The present invention virtually eliminates the risk of granting access to unauthorized users by determining identity from an analysis of a user's unique biometric characteristics. This also includes preventing users under a certain age from accessing or purchasing adult items or items limited to certain ages. The invention further enhances fraud resistance by maintaining authenticating data and carrying out the identity verification operations at a point in the system that is operationally isolated from the user requesting access, thereby preventing an unauthorized user from acquiring copies of the authenticating data or from tampering with the verification process. Such a system is clearly superior to existing token-based systems wherein authenticating information, such as biometrics or personal codes, is stored on and can be recovered from the token, and wherein the actual identity determination is potentially in operational contact with the user during the access process.

Further, the invention can be cost-effectively integrated with existing electronic transmission systems currently installed in corporate intranets and over the Internet.

These and other advantages of the invention will become more fully apparent when the following detailed description of the invention is read in conjunction with the accompanying drawings.

DETAILED DESCRIPTION

Figure 1:
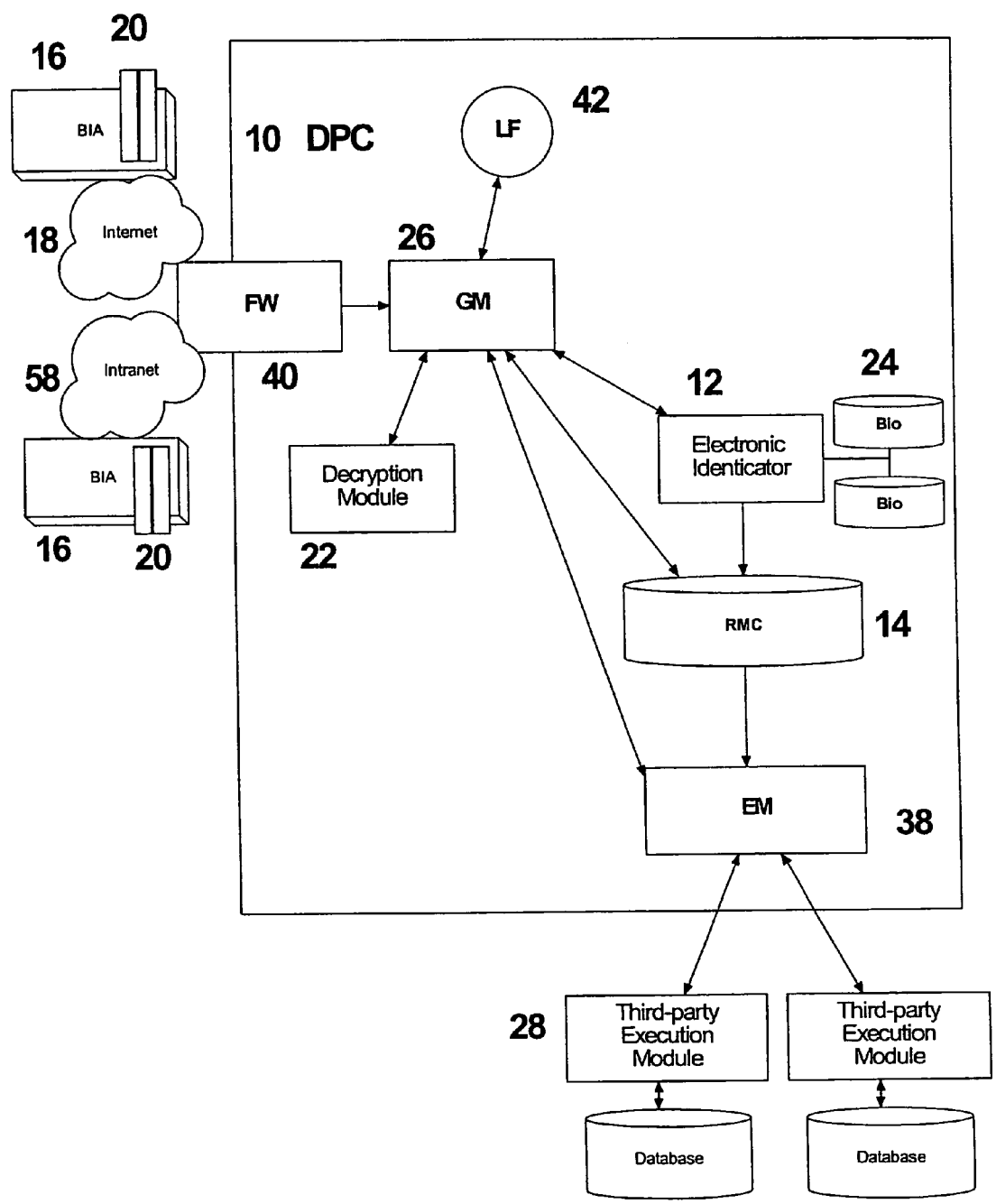
FIG. 1 shows a preferred embodiment of the invention having a biometric input apparatus that is connected a data processing center (DPC) through an Internet or intranet. The data processing center has an electronic identicator and a rule module clearinghouse.

The invention provides a tokenless biometric method and system for authorizing and executing electronic transmissions using a data processing center (DPC) 10, that has an Electronic Identicator (Identicator) 12 and an electronic Rule Module Clearinghouse (Clearinghouse) 14. The user forwards their biometric samples to the data processing center via biometric input apparatus (BIA) 16. Electronic transmissions of data, including the transmission of the biometric samples from the BIA to the DPC optionally occurs over an intranet 58, extranet or the Internet 18, whether using a local area network (LAN) or wide area network (WAN). It is the essence of this invention that the user not present any manmade personalized tokens during an identification process in order for an electronic transmission to be authorized. Such tokens include smart cards, magnetic swipe cards, or personal computers with resident user-customized data.

Tokenless biometric electronic transmissions are characterized by identifying the user with the user's bid biometric sample 62 submitted through an unattended, stand alone BIA 16 which is directly connected via dial-up, leased lines or wireless modem 56 to the Internet 18, or through a BIA 16 incorporated to any client terminal such as a desktop personal computer, a notebook computer, a thin-client, or other public terminal or kiosk 60 such as an Automated Teller Machine (ATM). In a preferred embodiment, the user is identified through biometrics and age verification, while third-party databases 28 which are accessed to complete the electronic transmission are identified through the verification of a digital certificate issued by an authorized certifying authority. The use of the word BIA used in this application refers to both the unattended stand alone BIA 16 and also to a BIA 16 incorporated to any client terminal.

Execution of a Rule Module (RM) 50 or an Execution Command (EC) 52 by the Execution Module (EM) 38 may result in a declined transmission due to lack of an identifiable third-party 28, a closed or inoperative third-party database 28, or some other immediately detectable problem condition. If the transmission is declined, the Clearinghouse 14 or the Identicator 12 transmits the decline notification back to the BIA.

In one embodiment, the BIA 16 is actually built-in and/or integrated with a personal computer, although the invention does not require that the personal computer contain any resident user-customized data, such as Pattern Data (PD) 54, Execution Commands 52 or private encryption keys.

In another embodiment, the third-party is a representative of a business entity or an actual business entity itself that has authorized the user to utilize the third-party databases 28 for data access, data processing or data presentation to complete the electronic transmission.

An electronic transmission is any transmission that allows for access of electronic data, processing of electronic data, or presentation of any electronic data. Such electronic transmissions may take many forms, including a user-customized electronic request for access to stored database content, an electronic request to personalize data using a digital certificate, or an electronic request to present or display data in a customized format. In sum, an electronic transmission is the accessing, processing, or presentation of any electronic data or content which does not in and of itself constitute or execute either an electronic financial transaction wherein the exchange or alteration of any financial assets occurs, nor an automated door lock or an automated physical site access mechanism.

Examples of electronic accessing of data include accessing databases with content or text, access to web sites, web site chat rooms. Internet educational courses, Internet games or game arcades, Internet examinations or tests, medical or health data, and Internet software. Other such data access includes other databases that require membership such as extent of insurance coverage, airline frequent flier rules, health club membership privileges, concert seats, movie rentals, check verification, and electronic voting. Other such data access includes age verification of the user for movie tickets, rentals and the like.

Examples of electronic processing of data include, intelligent search of the Internet 18 to locate information (Pull Data), such as the retrieval of investment data and news regarding a specific company, the retrieval medical news about a specific topic, the retrieval of price quotes for services or products, the retrieval of mathematical spreadsheets, emails, visual or graphic images, audible content, software code, computer software programs, Internet web sites, electronic instant messaging, and the like.

Pattern Data (PD) 54, as used herein, is any data or information which is customized to a particular user ("user-customized"). Such Pattern Data includes user-customized demographic information, user age information, user-customized Internet search or browsing preferences, user-customized purchasing patterns, and the like. It should be noted that user-customized is different from user-unique. Electronic data or electronic transmissions which are customized to a user, or "user-customized", have been customized by or for a user, but may not necessarily be unique to that user. Therefore, user-customized data which applies to one user may also apply identically to another user. However, electronic data or electronic transmissions which are unique to a user, or "user-unique", are distinctive and without equal, and hence are exclusive to that particular user.

An Execution Command (EC) 52, as used herein, is any computer software command which is associated with at least one Pattern Data 54.

Figure 5:
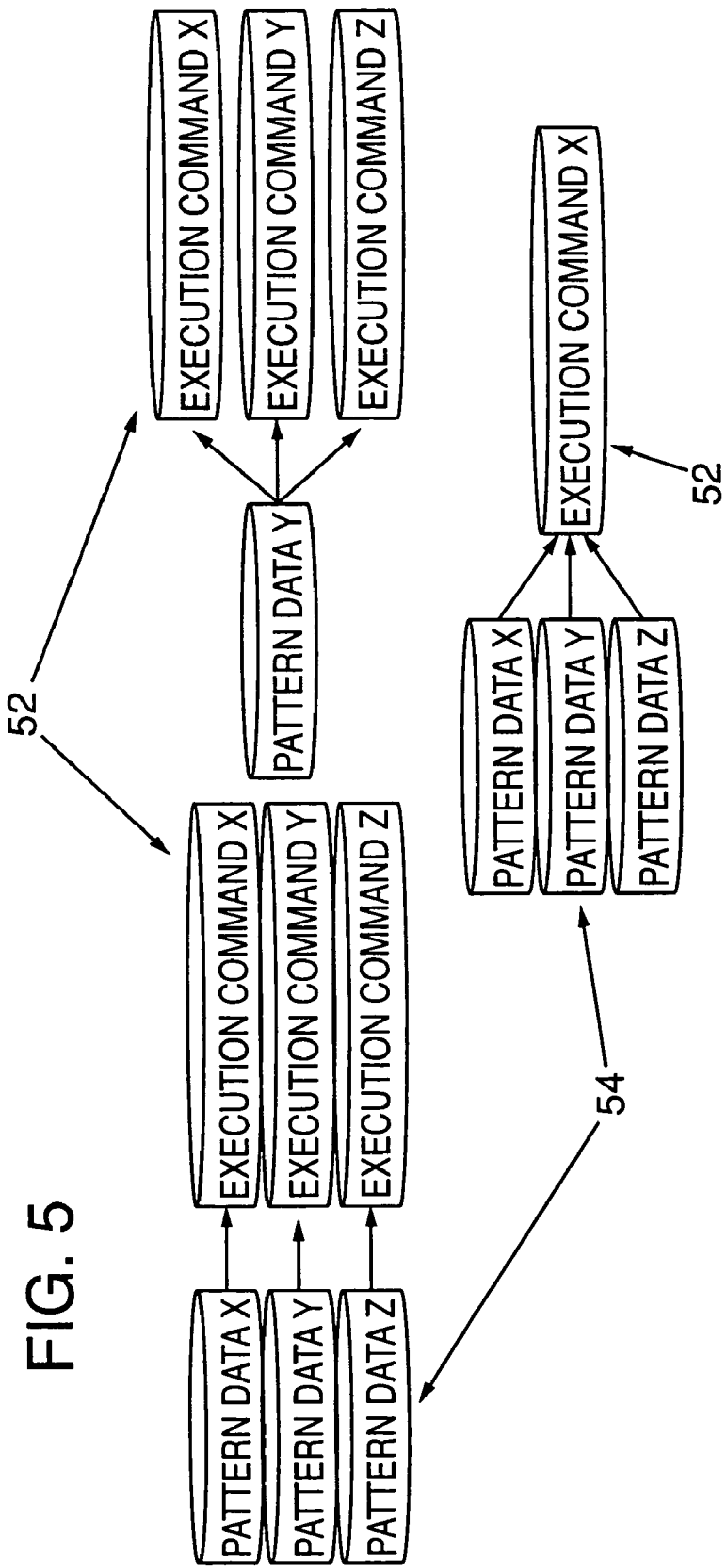
FIG. 5 shows various structures for association of pattern data and execution commands.

As shown in FIG. 5, a Rule Module (RM) 50, as used herein, is any conditional association between at least one Pattern Data 54 and at least one Execution Command, whereby if a Pattern Data 54 is invoked by a user, at least that one associated Execution Command 52 is in turn invoked by that Pattern Data 54 in order to execute at least one electronic transmission.

The Clearinghouse 14 is a database or registry of at least one Pattern Data 54 and at least one Execution Command 52 together forming at least one Rule Module (RM) 50, and has the capability to delete, add or edit associations between any Pattern Data 54 and any Execution Command to delete, add, edit, or invoke any Rule Module 50 in order to execute an electronic transmission.

The system used for identifying the user by their bid and registration biometric samples comprises the following components:

Biometric Input Apparatus ("BIA")
Communication lines
Electronic Identicator Server ("Identicator")

These components together allow a user to access, process or present an electronic transmission without the user being required to present any man-made memory token such as plastic or paper cards, or a personal computer with resident user-customized data.

Biometric Input Apparatus (BIA)

The BIA 16 is a device that gathers biometric samples from users. Each BIA 16 conducts one or more of the following operations:

gather biometric input or sample directly from the person of a user
gather a PIC code or password from a user
secure communication between BIA 16 and DPC 10 using encryption
secure storage of secret encryption keys
store and retrieve a unique BIA hardware identification code
secure enclosure & components from unauthorized tampering
present or display electronic messages and allows users to either view or hear an electronic transmission message
scan a magnetic stripe card
allow parties to select and edit electronic transmissions.

Biometric input is gathered using a biometric sensor 10 located within BIA 16. Biometric sensor 10 is a finger image sensor, however it is understood that other types of biometric sensors such as iris scan, voice print, retinal scan, facial scan and others are may be used.

For BIAs requiring a fingerprint sensor, the BIA 16 has a biometric fraud detection mechanism (not shown) that will assure that any biometric input gathered from the biometric sensor is from a real physical person, instead of a copy or replica. Preferably for the finger image sensor, this is a blood flow detector.

For systems employing a personal identification code (PIC), the PIC is gathered using a keypad or PIC pad 8 that is preferably located securely inside the BIA.

Communication security is provided by encryption using unique secret keys known only to that specific BIA 16 and the DPC, and the DES encryption algorithm, preferably triple-encrypted. Triple encryption means successive encrypt/decrypt/encrypt operations using two distinct 56-bit DES keys. This provides significantly higher security than a single encryption operation with one 56-bit DES key. Alternately, a public/private key system may also be used to encrypt information that passes between BIA 16 and DPC. Both DES and public key encryption is well known in the industry.

The BIA 16 also has secure memory that can store and retrieve the unique secret encryption keys used to enable secure communications with the DPC. In this embodiment, this is battery backed-up RAM that is set up to be erased whenever the tamper-detect circuitry reports that tampering has been detected.

To use encryption keys, a key management system must be employed to assure that both sender and receiver are using the same key. When using DES, a preferred key management system is DUKPT, which is well known in the industry. DUKPT is designed to provide a different DES key for each transmission, without leaving behind the trace of the initial secret key. The implications of this are that even successful capture and dissection of a BIA 16 will not reveal messages that have previously been sent, a very important goal when the effective lifetime of the information transmitted is years. DUKPT is fully specified in ANSI X9.24. The DUKPT key table is stored in the secure memory.

Each BIA 16 preferably has a hardware identification code that is registered with the Identicator 12 at the time of manufacture. This makes the BIA 16 uniquely identifiable to the Identicator 12 in all transmissions from that BIA 16. The BIA hardware identification code is preferably stored in write-once memory.

BIA physical security is assured by standard mechanisms. Preferably, these comprise tamper-detect circuitry, an enclosure that cannot be easily opened without visibly injuring the enclosure, erasable memory for critical secrets such as encryption keys, write-once memory for hardware identification, tight integration of all components, and "potting" of exposed circuitry.

Information such as the content of a transmission, the identity of a user, or other transmission-related information is displayed using an integrated LCD screen 6. It is preferable that the LCD screen be connected securely to the other components in the BIA 16 to maintain security. Approval or cancellation of a transmission is done using the BIA 16 keypad.

A magnetic stripe reader 20 is optionally used to read any information that is encoded on the magnetic stripe of a card. This is preferably used during initial registration of the user for efficient gathering of a user's registration with the DPC. Optionally, the BIA 16 also validates public key digital certificates. In one embodiment, public keys of a particular certifying authority are initially stored in the BIA 16 at the time of construction.

Although a preferred embodiment is described above, there are many different variations on specific BIA 16 implementations. Fundamentally any device that is secure, that can gather a biometric sample, and that can connect to the Identicator 12 via some form of communication line 18 can function as a BIA.

The BIA hardware identification code is not used to identify the user. However, once a user is identified by their biometric, the BIA hardware identification code optionally functions as Pattern Data 54 to invoke certain access often based on the user's age, processing, or display commands in the Clearinghouse.

It should be noted that a BIA 16 machine is any device that reads or scans a biometric sample 62 of a user. Example devices which incorporate a BIA 16 include wireless pagers, cellular and standard telephones, on-line network computer terminals, on-line exercise machines that are connected to and can be accessed through a communications network, on-line electronic books which can download electronic text from an Internet site, on-line automated teller machines that are connected to a communications network such as the Internet, on-line vending machines that are connected to the Internet 18 or an Intranet 58, on-line information terminals or public kiosks at airports which are connected to a communications network such as the Internet, on-line personal digital assistants such as Palm Pilots™, on-line photocopy machines that are either connected to a communications network such as the Internet 18 or an Intranet, automobile embedded Internet-connected appliances which download preferred radio stations, seat and temperature adjustments, and the like, household appliances such as refrigerators, microwaves, and the like that are connected to a communications network such as the Internet, home entertainment appliances including on-line television devices such as WebTV™, and compact disc audio systems and the like, which are connected to communications networks such as the Internet, along with their respective remote controls.

Registration/Enrollment

Figure 2:
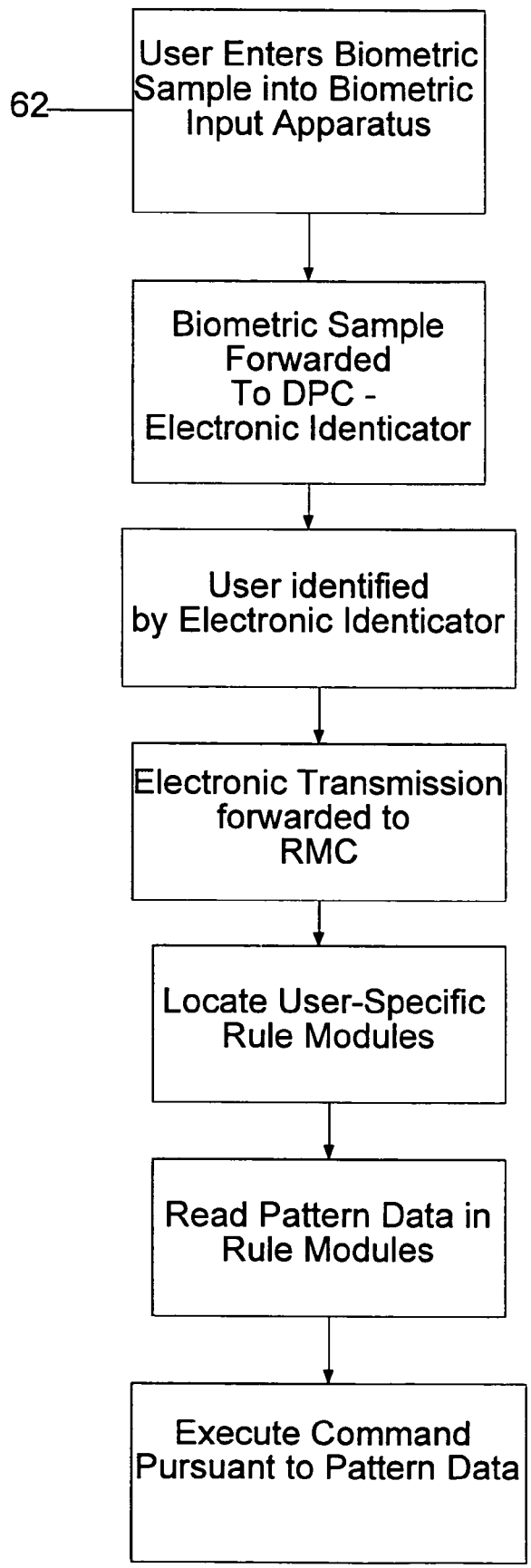
FIG. 2 is a flow chart of the process of submitting a biometric sample to the DPC until an execution command of the identified user is executed by the Execution Module.
Figure 3:
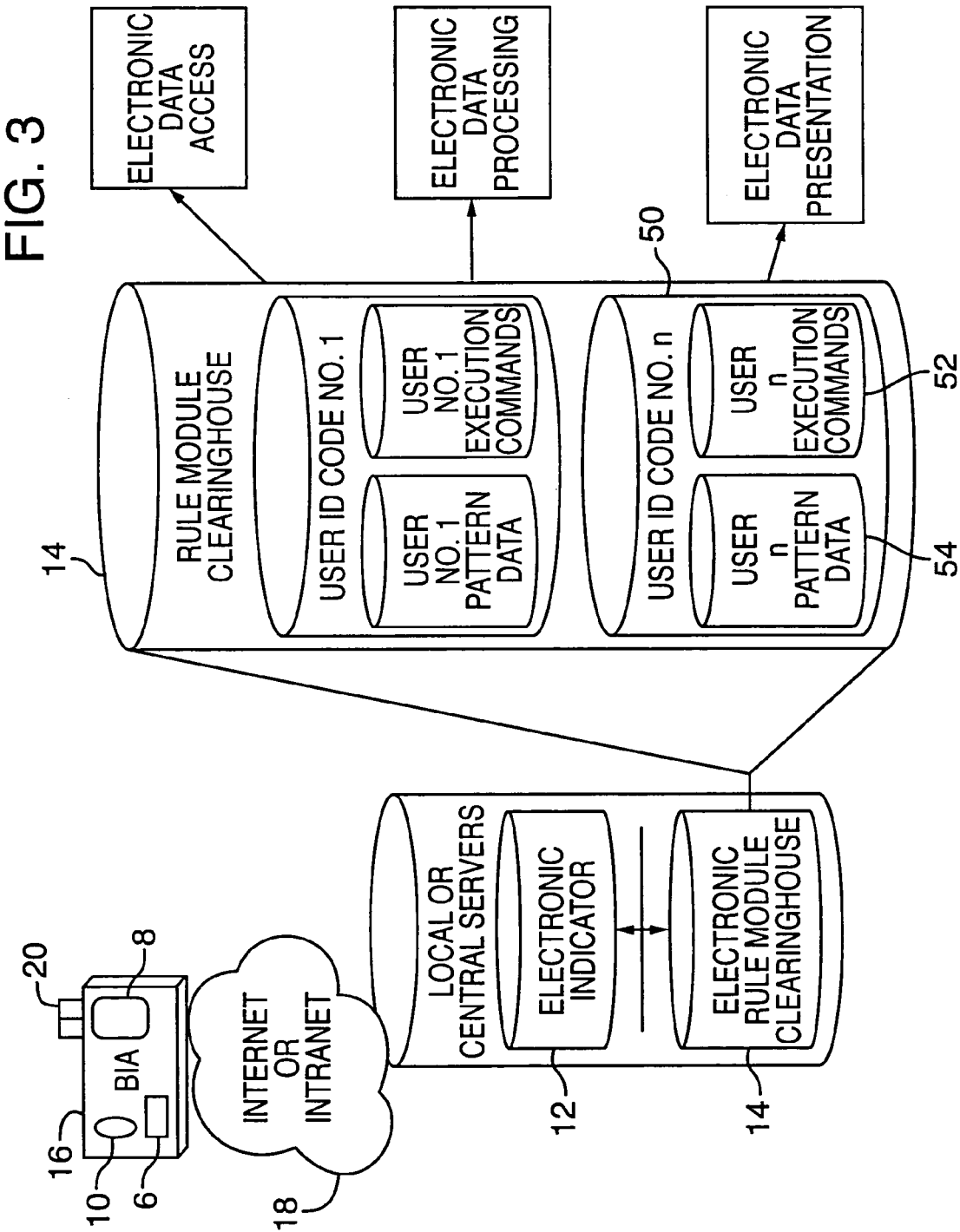
FIG. 3 shows the detail of the rule module clearinghouse with pattern data and execution commands in rule modules.

As shown in FIG. 2, a user typically registers at least one biometric sample 62 with the Identicator 12 via a BIA 16 device. Any user-unique biometric sample 62 can be registered including a fingerprint, a facial scan, a retinal image, an iris scan, or a voice print. Biometric samples gathered during the registration step are stored at the data processing center (DPC) 10.

In an additional embodiment, the network also has connections to a computer (PC) with a connected BIA and a wireless device with a connected BIA to allow users to perform functions in the system such as pre-enrollment, enrollment, and record maintenance. The system is also connected to at least one third party information database with which Electronic Identicator's can conduct user identity checks and age checks.

To enroll into the system of the invention, a user presents identity-verifying information and age-verifying information at a participating attended enrollment station with a BIA. In an additional embodiment, the user may also enter a PIC.

Users interested in registering in the system further have the option to pre-enroll. That is provide a partial enrollment, by providing only a portion of the required enrollment information for the invention's services via a computer, a vending machine, a wireless device, a kiosk, or a verifier device, which is connected to a network preferably but without limitation the Internet. Pre-enrollment records are stored as partial records which a user cannot use to verify their age until the remainder of enrollment information is collected and verified by an Electronic Identicator. Such partial records are marked pre-enrollment.

At the time of registration of users, each user is assigned a User ID Code that is unique and exclusive to each user. The User ID Code is automatically generated by the DPC 10 to validate that a user's bid biometric sample 62 has matched with that user's stored biometric sample. The User ID Code is not known to the user. Further, the User ID Code is different from the Personal Identification Code (PIC) of the user. The user's Personal Identification Code is known to the user, and it is optionally presented to the Identicator 12 by the user during the identification process to increase the security and efficiency of the DPC's biometric matches.

The user optionally registers user-customized data, such as the user's age, with the Clearinghouse 14 by the user. Examples of optional user-customized data include Pattern Data 54, an Execution Command 52 (EC), or a Rule Module 50 (RM). A Rule Module 50 comprises at least one Pattern Data 54 which is associated with at least one Execution Command. These data are stored in the Clearinghouse 14 and are optionally registered by the user, by the Clearinghouse 14, by an authorized third-party 28, or any combination of the above named parties.

Authorized third-parties 28 optionally register identification credentials with the Identicator 12, in order to enable the Identicator 12 to authenticate to a specific user that their electronic transmission has been correctly executed by the intended third-party.

Examples of authorized third-party execution of electronic transmissions include accessing data in third-party 28 databases or servers, processing data by third-party databases 28 or servers, presenting or displaying data to the user by a third-party database 28, or processing of data by the DPC 10. If the third-party is a person, the user may register a biometric with the Identicator 12. If the third-party is an entity, such as a corporation, it may register a digital certificate with the Identicator 12. Third-party digital certificates are available from certifying authorities, and they provide the assurance that the entity with the certificate is the authentic owner of that identity. These certificates contain readable text and other information that describes the entity. These certificates include corporate logos, a corporate address, as well as the company name.

BIA hardware identification codes are unique numbers assigned to BIA 16 devices at the time of manufacture. If an entity, such as a company, wishes all user-customized transmissions issuing from a given BIA 16 to be communicated to a particular intranet, the company registers any such BIAs with the Identicator 12, which updates the BIA 16 device records.

Preferably, the security surrounding the registration of an entity's digital certificates or of the BIA hardware identification codes with the Identicator 12 is extremely strong, as this is a potential source for large losses over a short period of time.

A user registers with the Identicator 12, and at least one Pattern Data 54 which include a biometric sample 62, a biometric-PIC or a user's age. To register, a user submits a registration biometric sample 62 provided by their physical person to the BIA. The BIA 16 determines that the biometric scan is non-fraudulent, and translates and compresses that biometric scan into a format suitable for rapid transmission to the Identicator 12. In a preferred embodiment, the scan is translated into a digital image. In another preferred embodiment, the user enters a PIC code into the BIA 16 keypad. The BIA 16 transmits the registration data and identification data to the Identicator 12. The Identicator 12 inserts the biometric (or biometric-PIC) into the appropriate Identicator 12 database and generates a User ID Code that is unique to the user. The age information of the user is then verified by the Identicator. From this point on, any time the user is identified by the Identicator 12, the user's User ID Code is forwarded to the Clearinghouse 14 and it invokes at least one Rule Module customized to that user. In the Clearinghouse 14 database, a Rule Module is created that is identified by the user's User ID Code. This enables the person to originate electronic transmissions.

In one embodiment, the Identicator 12 automatically assigns a new user-customized Clearinghouse 14 sub-database to a person's biometric, biometric-PIC, or User ID Code.

In one embodiment, there is a re-registration check step, wherein the user's registration biometric sample 62 is compared against previously registered biometric samples wherein if a match occurs, the computer system is alerted to the fact that the user is attempting or has re-registered with the Identicator.

Figure 6:
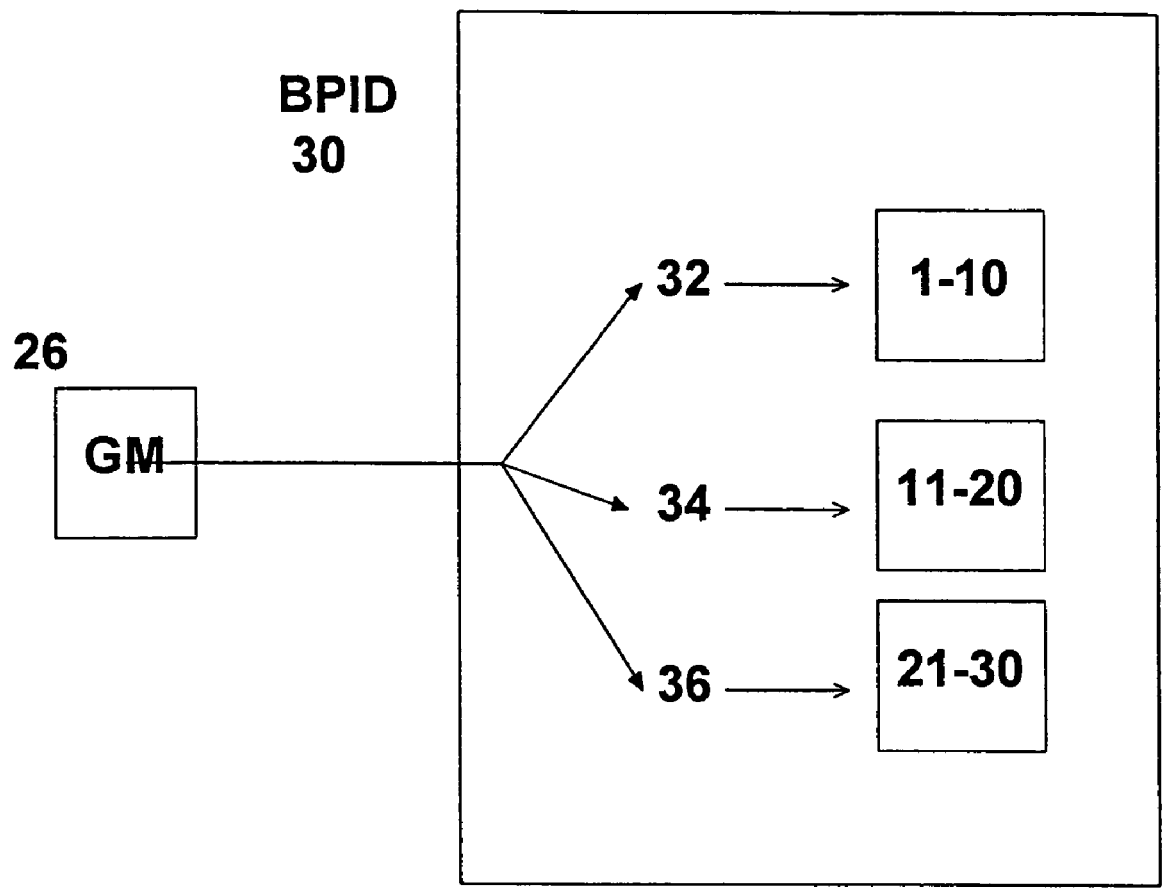
FIG. 6 shows the detail of an embodiment for search of a registered biometric sample database using personal identification codes.

In another embodiment where a PIC is used for identification purposes as shown in FIG. 6, a biometric theft resolution step is preferably employed, to change a user's PIC when it is determined that a user's biometric sample 62 has been fraudulently used or duplicated.

Subordinated User Registration

In this embodiment, a user registers with the DPC 10 as a primary user. This means that the primary user may restrict, modify, or otherwise control a subordinated user's electronic transmissions to access, process or present electronic data and electronic content stored on various third-party 28 Execution Modules 38 or third-party 28 databases. This may be desired, for example, when the primary user is a parent who wishes to influence or govern the on-line browsing activity of their minor child, who as the subordinated user is permitted access to certain desirable electronic databases while being denied access to undesirable electronic databases. In this embodiment of the invention, the primary user registers with the DPC 10 their biometric sample 62 along with the subordinated user's biometric sample 62. Separate and unique User ID Codes are issued by the Identicator for the primary user and the subordinated user, respectively.

Figure 4:
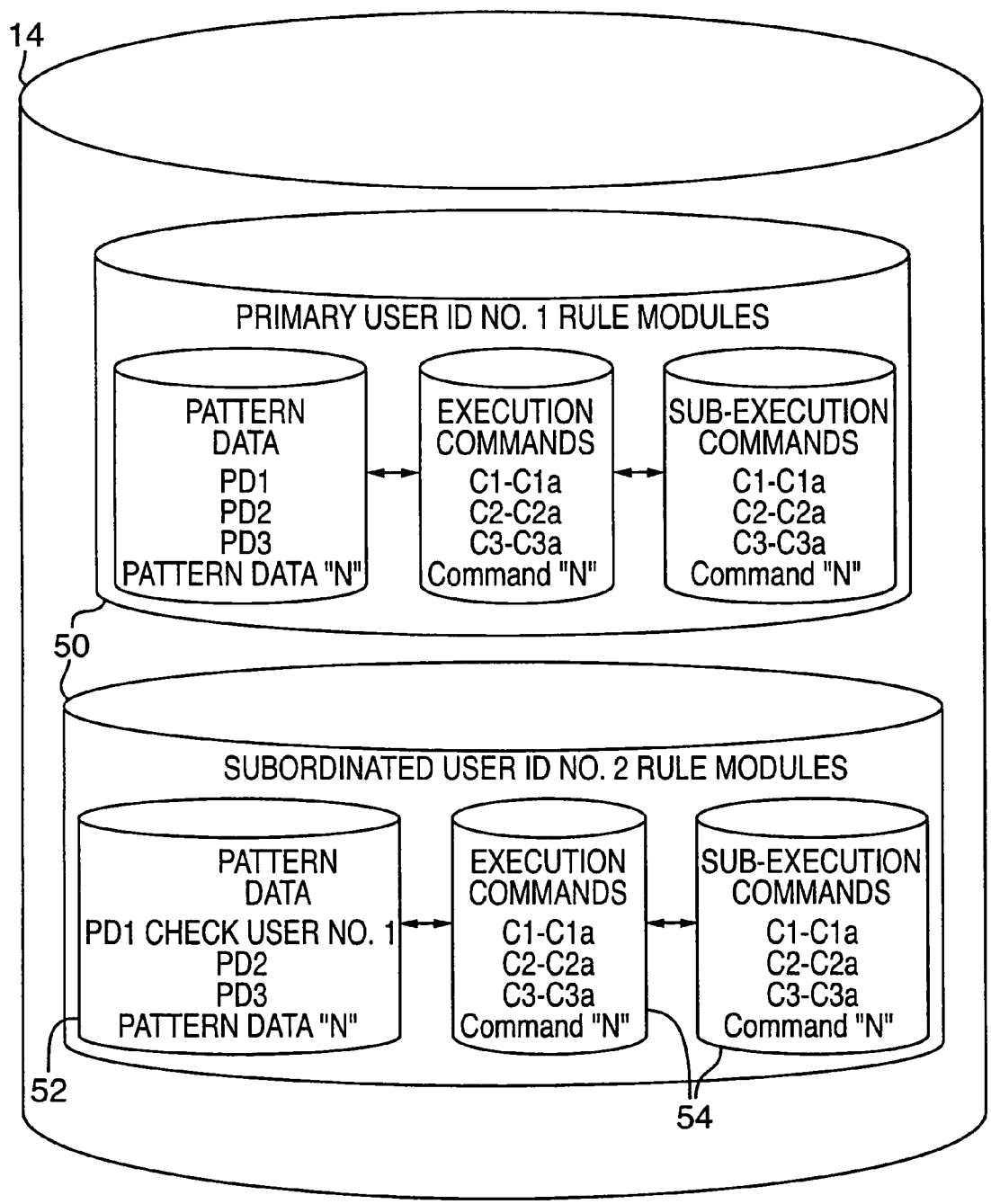
FIG. 4 shows the relationship between a primary user's rule module and a subordinated user's rule module.

Once the subordinated user logs onto a network and is identified by the Identicator, the subordinated user's User ID Code is forwarded to the Clearinghouse 14 to identify the subordinated user's customized Rule Modules 50. The Rule Module determines the age of the subordinated user and determines if it is below a certain number. As shown in FIG. 4. in a Rule Module 50 designated for the subordinated user, a Pattern Data 54 is constructed indicating that the user is in fact a subordinated user, and the associated Execution Command 52 dictates that the subordinated user's access limits, restrictions and priorities must be governed by Rule Modules 50 of the primary user.

In one embodiment a subordinated user is prohibited by the primary user's Rule Modules 50 from purchasing cigarettes and alcohol, or from accessing R-rated films being shown in theatres. The subordinated user's age is determined to be below 18. Therefore, the age of the subordinated user prevents the user from purchasing or accessing items for which one must be 18 or older. If the primary user's Rule Modules 50 are silent with respect to any particular subordinated user's requested electronic transmission, the subordinated user's relevant Rule Modules 50 will govern that electronic transmission and permit the electronic transmission to proceed unimpeded. In a different embodiment, a subordinate user may in turn have another subordinated user.

By way of illustration and not as a limitation, one way of presenting the age verification information of the subordinate during enrollment includes driver's license data being read from a magnetic stripe or bar code on the driver's license, from which date of birth information is pulled and used to calculate the user's age. Examples of suitable identity-verifying information are: a government ID number and state of issue, social security number, address, phone number, digital scans of information documents presented for identification, and other personal information about the enrolling user. This information may be card-swiped, scanned, hand-keyed, or entered by another means. In an additional embodiment, identity documents such as a driver's license or identification card are digitally imaged and stored in the respective user's record. Digitally imaging identity documents provides the system of the invention a security feature because it enables authorized individuals (such as verifiers and law enforcement) who challenge an age-restricted transaction verification to view the identifying documents a user used to enroll into the system.

Because a user's biometric is used for identification purposes, even if a subordinated user attempts to re-register with the DPC 10 under a different name, a search of previous registration biometric samples will show that the registrant has in fact previously registered with the DPC 10 and is a subordinated user.

Yet another embodiment of the invention comprises checking user age verification information against user age verification information that is already recorded in the system or purchasing information from private, public, or government databases. Examples of such information include, but are not limited to, driver's license data, employment data, and biometric data.

Communication Lines

Communications between the BIA 16 and the Identicator occur via many different communication methods. Most depend on the particular communication networks already deployed by the organization or retailer that deploys the transmission authorization system.

In an embodiment the BIAs 16 are connected via Ethernet to a local router, which is itself connected to a network operations center (NOC) via frame relay lines. At least one Identicator 12 is located at the NOC. Messages are sent from BIA 16 to the Identicator using TCP/IP over this network. In another embodiment, the BIAs 16 are connected via a cellular digital packet data (CDPD) modem to a CDPD provider, who provides TCP/IP connectivity from the BIA 16 to an intranet 58 to which at least one Identicator 12 is attached.

In yet another embodiment, a BIA 16 is connected via the Internet, as is at least one Identicator. TCP/IP is used to transmit messages from BIA 16 to Identicator. There are many different ways to connect BIA 16 to Identicator, both tethered and wireless, that are well understood in the industry, including but not limited to: the Internet; an intranet; an extranet; a local area network ("LAN"); and a wide area network ("WAN").

Data Processing Center

The Data Processing Center (DPC) 10 is comprised of an Electronic Identicator 12, a Rule Modules Clearinghouse 14, an internal Execution Module 38, a Firewall 40, a Decryption Module 22, a Gateway Machine 26, and a Logging Facility 42.

Electronic Identicator

The Electronic Identicator 12 (Identicator) serves to identify the user in an electronic transmission. The Identicator compares a user's bid biometric sample 62 with previously stored biometric samples from registered users, in order to identify the user. If a bid biometric sample 62 is successfully matched against a registered biometric sample, and the user is positively identified, the User ID Code which had been assigned to the user during initial registration will be forwarded to the Clearinghouse 14. The User ID Code transmitted by the Identicator 12 is used by the Clearinghouse 14 to locate the Rule Modules 50 that are customized to that user. In one embodiment, once the Electronic identicator identifies the user, the age of the user is also retrieved from the system.

As seen in FIG. 1, the Identicator 12 is connected to the Internet 18 or intranet 58 using a firewall machine 40. Messages are sent to a Gateway machine 26, which is responsible for overseeing the steps required to process the transmission, including forwarding the transmission to the Identicator 12 and the Clearinghouse 14.

Preferably, electronic messages transmitted between the BIA 16 and the DPC 10 are encrypted. For this, the transmission processor uses the Decryption Module (DM) 22, which utilizes the hardware identification code of the BIA 16 to identify the encryption codes that is required to decrypt messages from the BIA. Once decrypted, the identity of the user is determined using Identicator 12, which provides storage, retrieval and comparison of biometric samples 24 and age verification.

In an embodiment, during the user identification step, the Identicator requests the user to submit their PIC, and this PIC is used by the Identicator in combination with the user's bid biometric sample 62 for purposes of validating the identity of the user.

In another embodiment, the Identicator 12 provides periodic user re-identification queries. In this embodiment, in order for a user to extend an on-line session, the user is requested by the Identicator to re-identify themselves using any of the following: a user bid biometric sample 62 or Pattern Data 54, such as a personal identification code ("PIC").

In another embodiment, a third-party recipient of an electronic transmission is also identified by the Identicator using any of the following electronic verification means: a third-party ID Code, a digital certificate, an Internet protocol ("IP") address, a biometric, a hardware identification number, or any other code, text or number that uniquely identifies the third-party. In this way, the Identicator is enabled to provide the user with confirmation that the correct third-party received the electronic transmission. Examples include confirming that the correct web site or remote database was accessed by the user, that the correct third-party designee received the user's email or instant message, and the like.

In another embodiment, the Identicator 12 module is integrated with the Clearinghouse 14 (Clearinghouse) module.

In a preferred embodiment, more than one Identicator provides fault tolerance from either natural or man-made disasters. In this embodiment, each Identicator uses a backup power generator, redundant hardware, mirrored databases, and other standard fault tolerant equipment known in the industry.

Identification of the third-party and the user occurs using different methods, depending on the identification information that is provided by the BIA. The Identicator has subsystems for each type of information that is received by the Identicator, and each subsystem is highly optimized to provide rapid identification as outlined below.

In a preferred embodiment, Identicator 12 comprises subsystems that can identify parties from the following information:

biometric data and personal identification code (PIC)
biometric data alone
digital identification (digital certificates)
BIA hardware identification code
Biometric Identification Subsystem (BID)

In one embodiment of the Identicator, the BID subsystem comprises at least two BID processors, each of which is capable of identifying users only from their biometric sample.

In one embodiment, each BID processor contains the entire database of biometrics. To distribute the transmissions evenly across processors without undue effort, the Identicator determines randomly which BID processor will be used for a given electronic transmission, and delegates the identification request to that BID processor. That BID processor performs a search of its biometric sample database in order to find a matching registered biometric sample.

In another embodiment, other information is present that assists the BID processor in searching the database. For finger images, this includes information such as the classification of the image (whirl, arch, etc.), and other information about the finger ridge structure that is useful for selecting out biometrics that are not likely to match (or information on biometrics that are likely to match). Such biometric-based sorting and classification systems using mathematical algorithms, are known in the art for fingerprints and for other biometrics such as retina of the eye, voice print, and face vascular patterns.

Biometric comparisons are often more accurate if multiple biometrics are used. This includes the same type of biometrics from an individual such as fingerprint samples from different fingers, or different types of biometric samples such as a finger print and a voice print. In some embodiments, multiple biometrics are used to more rapidly and more accurately identify individuals.

Biometric-PIC Identification Subsystem (BPID)

As shown in FIG. 6, in a preferred embodiment, the BPID subsystem comprises at least two BPID processors, each of which is capable of identifying parties from their biometric and personal identification codes.

Preferably, the database of parties identifiable from biometric-PIC combinations is distributed equally across all BPID processors. Each processor is responsible for a subset of identifications.

The Identicator determines which Biometric-PIC from the BPID subsystem 30 is responsible for a given subdivision of the biometric database. In one embodiment, one BPID 32 is responsible for identifying people with PICs 1-10, another BPID 34 is responsible for identifying PICs 11-20, and a third BPID 36 is responsible for identifying PICs 21-30. For example, all messages from the BIA 16 containing a PIC that equals the number 30 would be routed to BPID 36 for identification of the user.

Once a BPID processor receives a bid biometric sample 62 and PIC for identification, the processor searches through its database, retrieving all registered biometric samples that match or correspond to that particular bid PIC. Once all corresponding registered biometric samples are retrieved, the Identicator 12 compares the bid biometric samples obtained from the electronic transmission to all retrieved registered biometric samples. If a match occurs, the Identicator transmits the identity of the user or the User ID Code to the Clearinghouse 14. If no match is found, the Identicator transmits a "not identified" message back to gateway machine 26 and to the logging facility 42.

Digital Identification Subsystem

In a preferred embodiment, the Digital Identification subsystem comprises multiple processors, each of which is capable of identifying a third-party from their digital certificates. In this embodiment, digital certificates are used to perform digital identification of a third-party. Preferably, these include corporate web site addresses and certifying authorities only. Where possible, computers provide digital certificates for identification of the computer and users use their biometrics for identification of the user.

Verifying that a particular digital certificate is valid requires a public key from the certifying authority that issued that particular digital certificate. This requires that the digital identification subsystem have a list of certifying authorities and the public keys used to validate the digital certificates they issue. This table must be secure, and the keys stored therein must be kept up to date. These processes and others relating to the actual process for validating digital certificates are well understood in the industry.

BIA Hardware Identification Subsystem (BHI)

In a preferred embodiment, BIA hardware identification codes are translated into third-party identification by the BHI subsystem. This subsystem maintains a list of all BIAs manufactured. Preferably, when a particular user uses a BIA, that user's geographic location is identified by their use of that particular BIA 16 during that electronic transmission session.

In another embodiment, the BIA hardware identification code does not serve to identify either the user or a third-party. This is the case in BIAs installed in public venues such as airport terminals, Automated Teller Machines in banks, or computers with BIAs for home use.

User ID Code

A User ID Code is an electronic message transmitted to the Clearinghouse 14, which informs the Clearinghouse 14 that a user has been successfully identified, and instructs the Clearinghouse 14 to invoke the Rule Modules 50 for that particular user.

Rule Modules Clearinghouse

In a preferred embodiment, once the user is identified by the Identicator 12, the User ID Code is forwarded to the electronic Rule Module Clearinghouse (Clearinghouse) 14 The Clearinghouse 14 instructs the Execution Module 38 to take the necessary steps for executing the Execution Commands 52 that are associated with the Pattern Data 54 registered with the Clearinghouse 14.

Rule Modules

The Clearinghouse 14 is comprised of at least one Rule Module 50 which is indexed specifically to one or more registered users (hence, "user-customized"). Therefore, the Rule Modules 50 are optionally not unique or exclusive to a single user. The Clearinghouse 14 functions as a central storage facility for registering, indexing, updating, and invoking various Rule Modules 50, and their software components, and to refine and improve execution of electronic transmissions according to user age, user-customized preferences and on-line activity patterns. Each of these Rule Modules 50 is composed of at least one Pattern Data 54 which is associated with or electronically linked to at least one Execution Command. As defined herein, user-customized does not necessarily mean that any Pattern Data 54 or the Execution Command 52 is unique to a user, but rather that they are indexed to or are assigned to a specific user. As such, the same Pattern Data 54 or Execution Command 52 may be assigned to several specific users, and hence would not be unique to any one user.

The Clearinghouse 14 optionally stores user-customized Pattern Data 54 that is unassociated with any user-customized Execution Commands 52 and optionally stores user-customized Execution Commands 52 that are not associated with any user-customized Pattern Data 54. Therefore, such unassociated Pattern Data 54 or Execution Commands 52 are optionally stored within the Clearinghouse 14 until they are associated with a Pattern Data 54 or an Execution Command 52 together thereby forming an executable Rule Module.

Once the user is identified by the Identicator 12, the User ID Code is forwarded to the Clearinghouse 14. The Clearinghouse 14 takes the User ID Code, optionally along with the BIA hardware ID code, the BIA 16 location data and the electronic transmission request, and searches among the user's customized Rule Module to invoke all of the Pattern Data 54 relevant to the electronic transmission being undertaken.

Pattern Data (PD)

As previously noted, Pattern Data 54 may be provided by the user while the Execution Command 52 for that Pattern Data 54 is provided by the Clearinghouse 14 or an authorized third-party, or the Pattern Data 54 provided by the Clearinghouse 14 and the Execution Command 52 by an authorized third-party 28, to form a single Rule Module 50.

Pattern Data 54 of a user is stored electronic data, which is customized to at least one user. A single Pattern Data 54 includes any of the following stored user-customized electronic data: a personal identification code, which is optionally alpha-numeric; demographic information; an email address; a BIA hardware identification code; a financial account; the user's date of birth; a secondary biometric; a non-financial data repository account; a telephone number; a mailing address; purchasing patterns; data on pre-paid accounts or memberships for products or services; electronic data usage patterns; Internet browsing patterns; employee status; job title; pre-set data on a user's current activity patterns; a digital certificate; a network credential; an Internet protocol address; a digital signature; an encryption key; an instant messaging address; personal medical records; an electronic audio signature; and an electronic visual signature.

In one embodiment the Pattern Data includes the user's date of birth. When the user requests access to an age-restricted item—for example, to purchase alcohol or tobacco, or to access an age-restricted movie—the system can compare the current date to the user's date of birth. Then, if the user is old enough, the system can grant the user access to the item; otherwise, the system can deny the user access.

In another embodiment, there is an automated age-restricted transaction. Using the Pattern Data, such an embodiment provides access to products/services that are governed by the same age restriction. A user enters their biometric and their PIC into the BIA. The user's information is sent to check that it matches the biometric records and age that the user entered in the BIA. Then the Pattern Data uses the age information to determine the restrictions on the user.

Although a User ID Code is optionally used as Pattern Data 54, the User ID Code is unique to each user and is not shared between users.

Execution Commands (ECs)

The Execution Commands 52 executed by the Execution Module 38 transmits electronic messages necessary for accessing, processing, or presentation of electronic data or content. Such transmissions include invoking a user's membership or eligibility for accessing insurance benefits (health, automobile, home, life, etc.), accessing travel service club benefits, accessing entertainment or travel event admittance, accessing electronic voting based on a user's place of residence, accessing electronic filing for taxes, and accessing privileges for permission to write paper checks or electronic checks.

In one embodiment, after the user has submitted their biometric information and it is verified, the age of the user is incorporated into the Execution Module's decision in what data content to transmit. If a user is over age 18, the Execution Module may access electronic voting based on the user's residence.

Additionally, these Execution Commands 52 include activation and invocation of a user's privileges for accessing, processing or displaying stored database content. Such content includes word-processing files, spreadsheet files, software code, graphics files, audio files, medical records; activation and invocation of a user's privileges for accessing, processing, or displaying on-line content-rich media, wherein such media includes, but is not limited to, age-appropriate Internet web sites, on-line audio or graphical content, electronic game content, on-line chat content, on-line messaging content, on-line educational content, on-line academic examination-taking, on-line personalized medical and health content, server-based computer software programs and hardware drivers.

In one embodiment, the Execution Command activates of the user's privileges based upon the age of the user. For example, if the user is over 18, the Execution Command allows the user to view adult web-sites.

Any Execution Command 52 is invoked by any Pattern Data 54 with which it is associated. Execution Commands 52 are user-customized instructions or commands which include Execution Commands 52 governing data access privileges, Execution Commands 52 governing data processing, Execution Commands 52 governing data display or presentation.

In another embodiment, the user-customized instructions are age-appropriate for the user. In a further embodiment, the Execution Commands governing data access privileges are based on the age of the user. The data access privileges are determined by retrieving the age of the user and determining the appropriate data access privileges based upon that age.

As shown in FIG. 5, in one embodiment, a single Pattern Data 54 is associated with multiple Execution Commands 52, thereby forming multiple Rule Modules 50. Also shown in FIG. 5 is another embodiment, where multiple Pattern Data 54 are associated with a single Execution Command, again forming multiple Rule Modules 50. Also shown in FIG. 5, another embodiment there is only one Pattern Data 45 associated with one Execution Command 52. Any user-customized Execution Command 52 may be provided to the Clearinghouse 14 by any of the following: the user, the Clearinghouse 14, or an authorized third-party.

In one embodiment, the user enters information into the system and the Electronic Identicator identifies the user. Once the user is identified by the Electronic Identicator, the Pattern Data of the Rule Module in the Clearinghouse can be accessed to determine the user's date of birth. If the current date shows that the user is old enough to perform an age-restricted transaction, then the transaction can be performed; otherwise, the user can be blocked from the transaction.

In a different embodiment, if the system determines that the user is too young to perform the requested type of transaction, the system rejects the user's request. In this embodiment an automated age-restricted transaction provides access to products, services, and/or areas that are governed by restrictions. The user enters their biometric sample into the BIA. In an alternate embodiment, the user also enters PIC that they registered with the system of the invention. Entering such a code may speed up and further secure the user record retrieval process. The user's biometric and the BIA identification code (ID code) are sent to a database, such as can be stored in the Clearinghouse. The user's sample biometric is used to find the user's system record. Once the user's record is found, if a Pattern Data checks a user's age, the age stored in the user's record is evaluated according to parameters indicated by the BIA ID code. If the user's age meets the ID code indicated parameters, the transaction is approved and indication of transaction approval is sent to the BIA. If, however, the user's age does not meet the ID code indicated parameters, the transaction is declined and indication of transaction decline is sent to the BIA.

In an additional embodiment, all age BIAs conduct transactions governed by the same age verification parameter(s). In such an embodiment, the user's age is verified according to system parameters of the Pattern data stored in the database of the Clearinghouse wherein the user's record is stored rather than evaluating the user's age by an unattended BIA code or action proposal code. In a further embodiment, the user's-age is verified according to system parameters stored in the database of the Clearinghouse wherein the user's record is stored.

There are several embodiments of user-customized Execution Commands 52 that govern access to electronic data such as web sites, web site content and databases. In one embodiment, an Execution Command 52 governing electronic transmissions for data access is a Universal Access Command (UAC) that is unique to the user. Each such Execution Command 52 is optionally invoked by the User ID Code serving as the Pattern Data 54. This Execution Command 52 is a software command that provides an authorized user access to any secured electronic data, such as those on third-party 28 databases. Invoking this Execution Command 52 enables the user to simultaneously access all Internet chat or messaging forums, web sites and on-line database content to which the user has authorization.

In another embodiment, the third-party being 28 contacted by the user for data access is also identified by the Identicator using public/private key cryptography. Once the third-party is successfully identified by the Identicator, this invokes a Rule Module in the Clearinghouse which is unique to this third-party and which is used to confirms to the user that the correct third-party database was accessed.

In another embodiment, the Universal Access Command is an Execution Command 52 that activates an on-line or Internet-connected device, such as a wireless pager, a wireless or tethered telephone, a network computer, an exercise machine that is connected to the Internet, an electronic book, an on-line public access Internet terminal, an automobile or household appliance that is connected to the Internet, an Internet-connected personal digital assistant such as a Palm Pilot™, an on-line photocopy machine, an Internet-connected digital audio player such as the Rio™. In such instances, the executed Rule Module renders the on-line or Internet connected device operational and permits the user that has gained access using their biometrics to conduct on-line activity to control or otherwise access the above mentioned Internet connected devices. For example, in one embodiment, an exercise machine incorporates a BIA 16 and is connected to the Internet. A user of the exercise machine enters their biometric sample, which is compared to registered biometric samples by the Identicator 12. Once the user is identified using their biometric samples, and the exercise device is identified using its hardware identification code, the Rule Module executes a command allowing the user to gain access to the exercise device. Optionally, additional Rule Modules 50 allow a user to save the details of their exercise activity (number of times, weight amount, date of exercise, etc.) on that exercise device as Pattern Data 54, in order to keep track of past performance and as a template for future exercise routines.

In another embodiment, an Internet-connected electronic book that incorporates a BIA is activated when the Identicator successfully identifies the user. This allows the user to download text and graphics of complete novels or films for which they have previously paid.

In another embodiment, a personal digital assistant, such as the Palm Pilot™, incorporates a BIA. When activated after the Identicator has successfully identified the user, the personal digital assistant permits the user to download and take on-line academic examinations. In another embodiment, an Internet-connected digital audio player such as the Rio™ incorporates a BIA 16. When activated as a result of successfully identification of the user by the Identicator, the audio player permits the user to download music for which they have authorization. Optionally, additional Rule Modules can track how many pages of the electronic book have been displayed and can retain a bookmark for the most recently read page. Optionally, additional Rule Modules can track how many times a downloaded electronic audio track has been played.

Upon the Identicator's successful identification of the user from their bid biometric and age verification with the user's age being over a certain number, other embodiments of Execution Commands 52 governing electronic transmission access include permitting the user to access their health insurance account and validate their benefits to a health-care provider prior to being admitted to a hospital, to access their pre-paid entertainment account and validate to admittance personnel their eligibility to attend an entertainment event, such as a live music concert on a pre-proscribed day, at a pre-proscribed time and to sit in a pre-proscribed seat, to access their video club account and validate to a merchant their eligibility to rent videos under their pre-paid membership, to access their driver's license on-line and validate to an authority their eligibility to drive a car, to purchase restricted products like alcohol or tobacco, or to access a restricted entertainment event such as an R-rated flint being shown in theatres, to access their credit rating account and validate to a cashier their eligibility for check-writing privileges, to access an Internet web site and enter a real-time chat worn with other people on-line.

Further embodiments of Execution Commands 52 governing electronic transmission access include entitling a user to extend an on-line user-customized session by repeating their user-customized session log-in by entering either their biometric or at least one of their user-customized Pattern Data 54 when periodically queried to do so by the Identicator 12 or Clearinghouse 14, to access customized radio or television programming, wherein the user can be provided with customized programming, with or without time restrictions, that reflects pre-designated preferences, such as a channel broadcasting only news on companies in which the user has an investment or a channel broadcasting only music from Broadway theater shows which the user has seen or indicated a desire to see, to access restricted portions of corporate intranet 58 databases on a selective basis, based upon pre-designated Pattern Data 54, such as the user's job title or company division, to access their travel reservations and validate to the admittance attendant that the user is eligible to travel, such as boarding a particular flight or a specific train, on a pre-proscribed day, at a pre-proscribed time, and to sit in a pre-proscribed seat, to access on-line position "papers" of user-customized political candidates and electoral ballot initiatives, and validate to an authorized third-party that the user is eligible to vote in particular elections after age verification, such as voting for a particular candidate running from a particular user-customized district.

There are several embodiments of user-customized Execution Commands 52 governing the processing of electronic data and electronic transmissions. Such Execution Commands 52 can govern: user-customized notification preferences for such electronic transmissions as real-time medical updates, pending Internet auctions, electronic stock trades and the like; user-customized instructions for user-location designating, for example, that the user may be located by third parties via whichever BIA 16 the user is using during an indicated time period, whereby the user can automatically receive their e-mails, instant messages, phone calls, faxes, and the like in real-time at the particular BIA 16 in use by him; user-customized travel customizations such as the user's preferences for lodging accommodations, travel costs, food, travel locations, and the like.

Further embodiments of user-customized Execution Commands 52 governing the processing of electronic data and electronic transmissions include: user-customized identity presentation preferences depending upon various pre-designated criteria such as the identity of a particular recipients, the user's sending location, and the like, whereby a user's preselected personal identifier, such as a distinct audio or visual sample, is electronically presented to a third-party recipient of the user's electronic transmission; invocation of user-customized Internet environment preferences, whereby a user's preferences are used to create a customized Internet web portal with the user's preferred search engines, bookmarks, and the like; user-customized data presentation preferences, whereby the priority, formatting and organization of displaying data is pre-designated by the user; user-customized customization of Internet search engines, and; user-customized customization of intelligent data tracking and extrapolating agents.

In one embodiment of an Execution Command 52 governing the processing of an electronic transmission, the user-customized Internet search engine is customized to locate, retrieve and present electronic transmissions for the user using an intelligent tracking and extrapolating agent. In one embodiment, the user's customized Rule Modules 50 provide instructions that even when the user is not logged onto a network, the Pattern Data 54 and Execution Commands 52 are periodically and automatically executed, added, changed or deleted based on the user's previous BIA 16 and on-line usage patterns. As a result, the user-customized search engine is automatically and progressively refined and customized to the user's evolving preferences and on-line activity patterns as tracked and interpreted by the user's own electronic, automated intelligent agent.

As an example of the above, the user's intelligent agent can direct the user's search engine to automatically conduct periodic, customized on-line data retrievals reflecting user-customized priorities for: product or service promotional offers or discounts via email or instant messaging; user-customized investment updates; user-customized medical or health information; competitive product or service pricings across a broad range of on-line merchants; hobby or recreational interests; interactive user-customized on-line advertisements, wherein product or service providers are permitted to provide unsolicited information to a user based upon certain user customized criteria; on-line event calendaring, wherein a user is automatically notified of upcoming events or activities reflecting their interests.

Further, the intelligent agent can extrapolate from the user's existing preferences and on-line activity patterns to automatically and periodically recommend to the user new data that may expand or delete the user's Pattern Data 54 and Execution Commands 52 based upon the intelligent agent's algorithmic projection of what the user's on-line preferences and activities will be in the future. For example, the intelligent agent can recognize that a user is interested in age-restricted services, and can generate a Pattern Data 54 that examines the user's date of birth.

In another embodiment, an Execution Command 52 functioning as an intelligent tracking and extrapolating agent centrally integrates data on the user's Internet browsing to provide user-customized recommendations on new products and services available from any number of Internet web sites or Internet merchants. Examples include the Execution Commands for retrieval of new types of music, books, and investment opportunities that reflect the user's age and preferences, but that such recommendations are pre-selected based on the Execution Command 52 having automatically conducted competitive price-comparisons from various third-party databases. In another embodiment, an Execution Command 52 integrates user-customized data from a user's calendaring or scheduling software program to provide the user with customized recommendations on user-customized offering for products, services or upcoming events based on the user's pre-scheduled activities in their on-line calendar.

In another embodiment, an Execution Command 52 appends a customized, user-customized audio or visual identifier which accompanies an electronic transmission for presentation to the recipient. This identifier is appended to the user's electronic transmission as a form of "electronic personal signature" to readily notify the recipient that the authenticated user sent the message. This identifier may be a unique biometric image or biometric sound sampled from the user, or it may be a non-biometric, distinct graphical or audio sample selected by the user to reflect their personal preferences, such as a cartoon image or a favorite sound or audio tone.

In another embodiment where greater security is required, an Execution Command 52 governs the appending of a user-unique network credential or digital certificate to an electronic transmission. If a user employing a biometric seeks to append their digital certificate to an electronic transmission, the user stores at least one command to sign electronic documents using their private keys, which are themselves centrally stored on a Clearinghouse 14 server. As such, the user's private keys are invoked as a header for the user's electronic transmission which, in combination with the electronic document itself and an MD5 calculation of the document, together form a digital signature. At a later time, an authorized recipient can use the user's public key from the DPC 10 or a third-party certifier to verify the authenticity of the sender and the electronic document's contents to yield a secure, authenticated electronic transmission. In this way, users do not have to manage their own private keys, nor do they have to retain physical possession of their digital certificates via smart cards or personal computers with resident user-customized data. In one embodiment, public keys of a particular certifying authority are initially stored in the BIA 16 at the time of construction.

In another embodiment, an Execution Command 52 governs the processing of an on-line, user-customized calendaring program or Internet calendaring web site, wherein the user's on-line scheduling calendar is automatically updated by the user-customized search engine and the user-customized intelligent search and tracking agent based upon user-customized Pattern Data 54. This could include, but would not be limited to, automatically updating the user's on-line calendar based on upcoming: user-customized entertainment events, user-customized business seminars, user-customized airline discounts to the user's preferred destinations, user-customized candidate and elections bulletins, and the like.

In another embodiment, the user pre-designates Execution Commands 52 governing the processing of electronic transmissions which filter the access and presentation of data when the user is subordinated user who is co-registrant or legal dependant of the primary user himself. Examples of such subordinated users could be the children or the spouse of a user. Examples of such access and presentation, or viewing, filters may be restrictions pre-designated by the primary user governing: subordinated user access to Internet web sites with adult or violent content; subordinated user access to on-line television or radio programming with adult or violent content; subordinated user access to the Internet 18 with restrictions covering on-line session length; subordinated or age-restricted user access to educational on-line resources which are automatically "pushed" to the subordinated user during a particular on-line session, as pre-determined by the primary user, in order to pro-actively circumscribe the content which a particular subordinated user is permitted to view or download. For example, a subordinated user's age can be determined using Pattern Data by comparing the current date with the user's date of birth: access to age-inappropriate materials can be denied if the subordinated user is not old enough.

In another embodiment, an Execution Command 52 provided to the Clearinghouse 14 by an authorized third-party, such as a user's employer, governs the processing and prioritization of electronic transmissions to the user on an intranet 58. As such, the Execution Command 52 determines which electronic transmissions are automatically "pushed" to the user during a particular on-line session, as pre-determined by the authorized third-party, in order to pro-actively circumscribe the content which a particular user is permitted to view or download Embodiments of user-customized Execution Commands 52 governing the display or presentation of electronic transmissions include controlling the organization and prioritization of on-line content such that text, audio and graphics are displayed according to a user's pre-determined preferences. This includes displaying informational updates in a certain prioritization order, wherein user-customized regional news may be presented prior to national or international news, displaying expenditure records in user-customized categories which reflect anticipated tax deduction categories, such as home improvement expenses, charitable contributions, and the like, displaying customized user-customized Internet web sites or portals, including the user's pre-designated bookmarks, preferred web links, calendaring programs, email mail addressing rosters, multiple email accounts with their accompanying inbox messages, user-customized instant messaging "buddy" lists.

Other embodiments of user-customized Execution Commands 52 governing the display or presentation of electronic transmissions include: displaying accrued user-customized consumer rewards incentives or customized on-line advertising according to a user's prescribed priorities, such that skiing apparel is presented to the user at a time based on their calendaring program's designating their scheduled winter vacation or such that an advertisement for new coffee flavors from the user's preferred vendor is presented during the user's morning log-on session; displaying the user's customized fitness program on an Internet-connected exercise machine, whereby the user is reminded of the number of repetitions the user performed at what difficulty level during their last exercise session, and thereby also presents a recommended number of repetitions and a recommended difficulty level for the user's current session.

Other embodiments include Execution Commands 52 governing: presentation or display filters which circumscribe what text, graphic or audio content the user is permitted to view; presentation or display filters which govern which products or services a user is permitted to purchase, such as a subordinated user whose parent is a primary user, and where the user under a certain age and a subordinated user are prohibited from purchasing cigarettes, is limited in their selection of on-line merchants, is limited in the amount of on-line session time the user is permitted to have in a single day, and the like.

Preferably, each identification request and each transmission request, whether successful or not, is logged in the Logging Facility (LF) 42.

In one embodiment, an age-restricted transaction is conducted at an unattended BIA that provides access to products, services and/or areas that are governed by different age restrictions. Such an embodiment allows for goods/services with either a single age restriction or varying age restrictions to be vended at the same BIA or network of BIAs. The user enters their biometric sample and at least one age-restricted action proposal. In an alternate embodiment, the user also enters a PIC that they registered with the system of the invention. An age-restriction action proposal involves the user selecting an age-restricted action to perform at the unattended BIA. A user makes an action proposal by one of various methods, such as pressing a button on one of the devices, selecting an image displayed on a touch screen display, or entering an alphanumeric code into a keypad on the device.

An example of such an action proposal is a user entering a cigarette selection code at a cigarette vending device comprising a BIA.

The user's biometric and the proposed action are sent to the central database. In an alternate embodiment, additional transaction information is transmitted from the BIA to the database of the Clearinghouse including but not limited to a BIA ID code, transaction type, transaction reference number, a transaction time, and station location.

The user's biometric record is found. If the user's biometric sample and the user biometric record match, the age associated with the matching biometric record is evaluated. The age is evaluated according to the parameters indicated by the age-restricted action proposal(s) sent to the database. If the user's age is acceptable, the user's age is verified, the age-restricted transaction is approved, and the user is notified. However, if either the biometric data does not match or the age associated with a matching biometric does not meet age-restricted action proposal parameters, the age-restricted transaction is not approved and the user is notified of the decline.

If the user has selected more than one action within the system (e.g. purchase beer and purchase cigarettes), the BIA sends the respective action proposal for each age-restricted item/service the user selects. During age verification, the user's age is evaluated according to the parameters associated with each action proposal. In such an embodiment, it is possible that the user's age is approved for accessing certain goods, services, and/or areas, but not for accessing others. This embodiment allows users to perform age-restricted actions for which their age qualifies at BIA offering multiple age-restricted actions with varying age restrictions and allows various types of age-restricted actions to be offered. By way of illustration and not as a limitation, a user might request purchase a pack of cigarettes, and pre-purchase a certain amount of beers for the night, all with one unattended age verification upon entry into the night club.

In a preferred embodiment, more than one Clearinghouse 14 servers provide fault tolerance from either natural or man-made disasters. In this embodiment, each Identicator uses a backup power generator, redundant hardware, mirrored databases, and other standard fault tolerant equipment known in the industry.

Rule Modules and Electronic Transmissions

Figure 8:
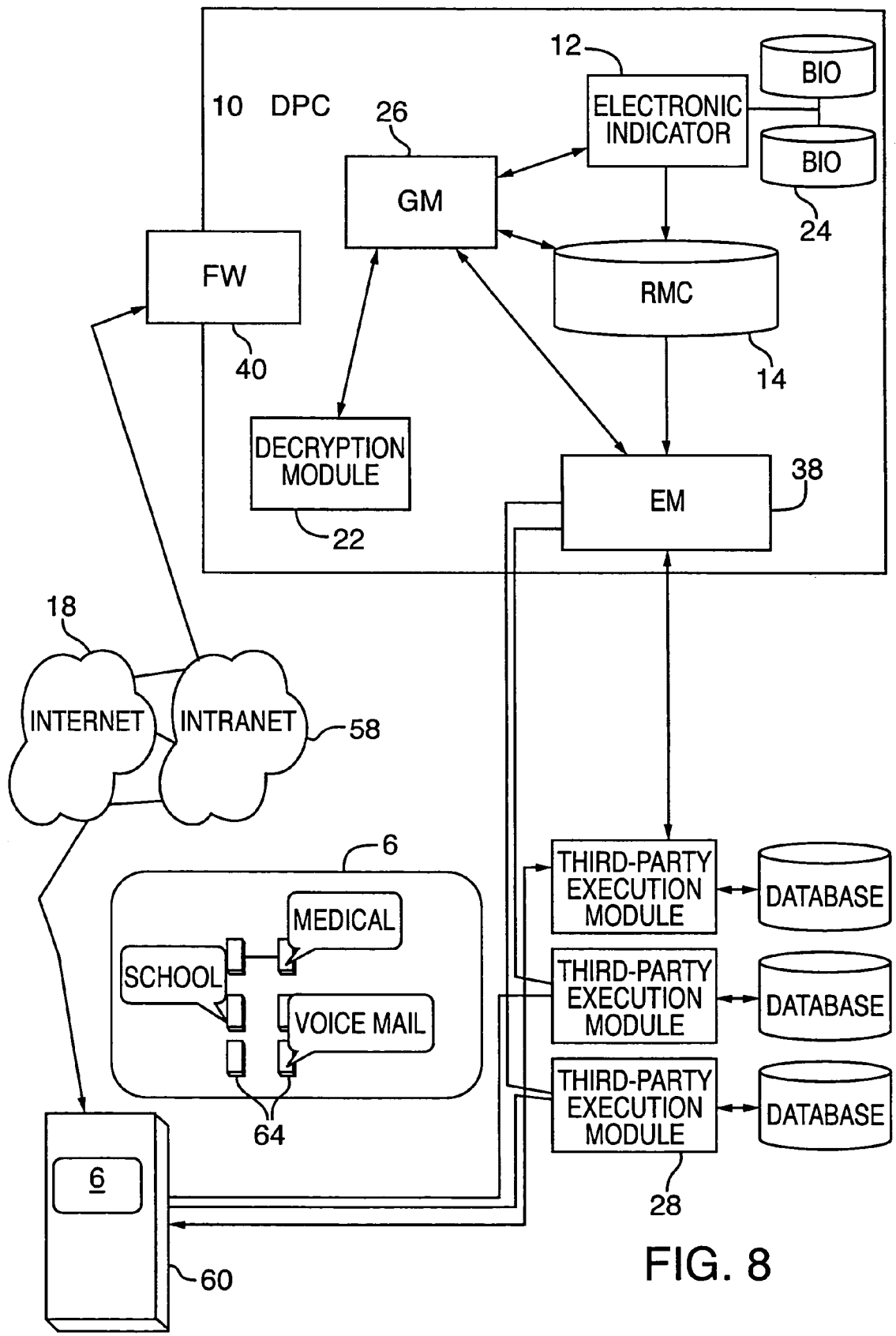
FIG. 8 shows an embodiment of the invention with a public terminal kiosk having a biometric input apparatus and the transformation of that public terminal kiosk into the user's personal Internet access site.

A specific embodiment of how Pattern Data 54 is used in conjunction with Execution Commands 52 is shown in FIG. 8. A user logs on by submitting their biometric to a BIA incorporated into a public kiosk 60. In this embodiment, the public kiosk itself is a computer terminal containing a networked thin-client and a web browser (collectively referred to in this embodiment as the "kiosk"). The BIA 16 forwards the user's bid biometric sample 62 to the DPC 10 for identity verification. Once the user is successfully identified by the Identicator 12, the user's User ID Code is forwarded to the Rule Modules Clearinghouse 14. Optionally, the BIA 16 also forwards its BIA hardware identification code to the DPC 10 for identification of the BIA 16 by the Identicator 12. In this embodiment, once the BIA 16 and the user are successfully identified, the BIA hardware identification code is forwarded to the Clearinghouse 14 along with the user's User ID Code. The Clearinghouse 14 is able to geographically and electronically locate the user via either the BIA hardware identification code, or the Internet Protocol (IP) Address (well known in the art).

Once the user logs on to the BIA 16 at the kiosk 60 and is successfully identified by the Identicator, the DPC 10 forwards the user's Universal Access Command to the BIA. The Universal Access Command identifies all third-party Execution Modules 38 and databases 28, along with the third party's Internet locations, denoted as IP Addresses or Uniform Resource Locators (URLs) and the like, to which the user has access privileges.

In one embodiment, the user enters their biometric and PIC. The user PIC is sent to the Clearinghouse. The Clearinghouse finds at least one potential biometric match for the user's biometric sample, finds the age mapped to the potential biometric match, and returns the potentially matching biometric(s) and the associated age(s) to the BIA. The Identicator determines whether or not the potentially matching biometric(s) matches the user's biometric sample. If a returned biometric record matches the user biometric sample, the age associated with that matching biometric is evaluated and the user is granted an age-restricted access level. The user makes their selection(s), and the transaction is approved if the user's selection(s) meets the pre-determined access level associated with their matching biometric record. If the user's biometric sample does not match a biometric record, the age-restricted transaction is declined. Additionally, if the user attempts to access a product, service or area that is not allowed in their pre-determined access level, the transaction is declined.

In an alternate embodiment, additional transaction information is transmitted from the BIA to the Clearinghouse or Identicator databases including but not limited to transaction type, transaction reference number, a transaction time, and terminal location. User financial account selection information can also be transmitted to the central database in a system which comprises biometric authorization of financial transactions. In this embodiment, the financial account selection indicates the user's registered financial account they would like to use for purchasing the age-restricted goods/services.

In an embodiment, the DPC 10 forwards to the kiosk 60 a user-customized display, presenting visual icons representing URLs for viewing by the user via the kiosk screen. In this embodiment, the following icons are presented to the user: a "Calendaring" icon, representing the user's centralized scheduling programs and customized scheduling; a "Messaging" icon, representing the user's centralized Internet accounts for email, voicemail, and fax; an "Academics" icon, representing the user's private academic coursework examinations account; a "Medical" icon, representing the user's centralized private health and medical records; a "Reading" icon, representing the user's centralized electronic books accounts; a "Games" icon, representing the user's centralized Internet game accounts; a "Word Processing" icon, representing the user's centralized accounts for word processing programs and user-edited content, and; a "Buddy List" icon, representing the user's centralized instant electronic messaging accounts.

The DPC 10 forwards to the BIA 16 a unique, one-time usage Random Key Number (RKN), optionally one for each and every one of said third-party database 28 Internet locations which are relevant to the user. The BIA 16 will store the Random Key Number in Random Access Memory (RAM), and will erase them when the user's log-on session terminates. These Random Key Numbers are preferably sent from the DPC 10 to the BIA 16 as encrypted 128-bit random number. The BIA 16 decrypts the Random Key Number and forwards it to the kiosk. At this point, the kiosk is permitted to display or present all such URLs for the user as text or—preferably as visual icons.

Note the user may have previously designated his Rule Modules 50 in the Clearinghouse 14 to display any or all such third-party database 28 locations in a grouped manner. In this embodiment, for example, the user's Rule Modules 50 may designate that all email, voicemail, and fax URLs be grouped together and represented by the presentation of a single "messaging" icon or graphic.

In this embodiment, when the user clicks on a particular icon and seeks to log into a particular URL third-party database, or to all of the URL third-party databases 28 represented by that icon, the kiosk 60 or the DPC 10 sends the Random Key Numbers to all of the respective URLs designated by the icon, along with the user's electronic transmission request. Execution Modules 38 located at each of these URLs query the DPC 10 to validate the Random Key Number it has received. If the DPC 10 confirms that the Random Key Number is current and valid, the DPC 10 invokes each Execution Module 38 pertinent to all of the user's relevant URL account number and access privileges for that third-party database. The DPC 10 provides this data to the URL, along with validation of the Random Key Number. In this way, the user is automatically permitted by each of the respective URL Execution Modules 38 to access that URL and its third-party databases.

Also in this embodiment, the user's Rule Modules 50 specify that the BIA 16 location may be used by the Clearinghouse 14 to enable the Clearinghouse 14 to automatically customize certain electronic transmissions for the user in real-time. For example, in this embodiment, the user clicks on the "Calendaring" icon. The kiosk requests the DPC 10 to access the user's Rule Module in the Clearinghouse 14 governing customized scheduling data. The relevant Rule Module 50 uses the BIA's location along with the user's Rule Modules 50 to access third-party Execution-Modules 38 and databases 28 that optionally forward to the kiosk user-customized, geographically-specific scheduling data for presentation to the user. Such scheduling data includes where in the local area the user can find their pre-registered preferences for culture, travel accommodations, and business manifested in locally available radio stations, hotels, films, theatres, museums, business events, companies in which the user might be interested, book readings, university lectures, friends whom the user may want to contact, and local sales calls the user may wish to make. Further, the user's calendaring priorities, highlighting local appointments, can be displayed for their review. In this way, the user is immediately familiarized with the locality in which the user finds himself using a BIA, with the scheduling data automatically reflecting their customized, personal priorities.

In this embodiment, the user's Rule Modules 50 stipulate that even when the user is not logged onto a network, certain of the user's Rule Modules 50 are to function on an automated basis, such as periodically updating the DPC's central retrieval of the user's email, voicemail and fax messages. In this way, when the user does actually log-on seeking to access this data, it is also available from the DPC 10 in real-time.

Further, in this embodiment, the user on the "Messaging" icon to access all of their email, Internet fax and Internet voicemail messaging accounts. The "Messaging" icon represents all of the URLs related to the user's messaging accounts which have been grouped by the Clearinghouse 14 according to the user's Rule Modules 50. The user has previously stored with the Clearinghouse 14 their messaging account URLs along with their respective account names and passwords. Once the user clicks on the kiosk's "get new messages" icon, the kiosk requests the DPC 10 to access the user's messaging accounts. Once this request is received by the DPC, the Clearinghouse 14 invokes the user's Rule Modules 50 governing message requests. Assuming the user wants to simultaneously obtain all of their messages at once, the DPC 10 in turn sends a HyperText Transfer Protocol (HTTP) "get" message command for each URL, thereby enabling the DPC 10 to retrieve all of their email, Internet voicemail and Internet fax account messages at once. (Note that HTTP is the protocol currently used to transfer information from Internet third-party databases 28 to client browsers.) These messages are the Pull Data retrieved by the DPC. The DPC 10 filters the HyperText Markup Language (HTML) to retain only user-relevant message contents and forward this to the kiosk for presentation to the user.

In the embodiment, the user also seeks to simultaneously retrieve their standard voicemail messages. This can be accomplished by the user storing their voicemail account numbers and respective passwords as part of Execution Commands 52 in the Clearinghouse. Once the user signals the kiosk to "get standard voicemail messages", this request is forwarded to the DPC 10 which places dial-up calls to the relevant voicemail systems in order to record and digitize the voicemail message playbacks. The DPC 10 forwards these messages to the kiosk for presentation to the user either as text or real audio.

In this embodiment, one of the user's invoked Rule Modules 50 that provide calendaring functions, the kiosk automatically presents the user with an age-appropriate "Academics" icon for notification that they must complete their university's on-line coursework examination. In this embodiment, the DPC 10 provides the BIA 16 with a packet containing the Universal Access Command, the Random Key Number, and any other relevant user-unique network credentials for the university's restricted database. The BIA 16 decrypts this packet and forwards it to the kiosk for display to the user. The user clicks on the displayed icon representing the URL for the third-party Execution Module 38 and databases at which resides the examination for which the user has pre-registered. The kiosk forwards Random Key Number to the URL, and the resident Execution Module 38 queries the DPC 10 to authenticate the validity of the Random Key Number. If the DPC 10 confirms the validity of the Random Key Number to the URL, the user is enabled to access the third party database and take their electronically stored course exam. Preferably for security, this particular Random Key Number would be good for only one on-line session by the user with the relevant third-party database, in this case being the university server on which is stored the course examination.

In this embodiment, the user also clicks on the "Medical" icon—to access their private health records in order to check on medical tests which their physician had completed that morning, along with accessing a customized collection of current medical news. Preferably, while the user was logged off, the user's relevant Rule Module automatically and periodically directed the Execution Module 38 to collect this data from third-party databases 28. In this instance, the DPC 10 provides the BIA 16 with a packet containing the Universal Access Command, the Random Key Number, and any other relevant user-unique network credentials for each third party database 28 containing the user's medical records and health news updates. The BIA 16 decrypts this package and forwards the data to the kiosk for display to the user. The displayed "Medical" icon represents the URLs of the respective third-parties' Execution Modules 38 and databases at which resides the user's customized medical information. The kiosk forwards a Random Key Number to each of said URLs, and the respective Execution Modules 38 query the DPC 10 to authenticate the validity of each of the Random Key Numbers. For each Random Key Number validation provided by the DPC 10 to the respective URL, the user is enabled to access the respective third party database for presentation of the user's private medical data.

Additionally, in this embodiment, the user clicks on the "Reading" icon to access third-party databases 28 storing certain electronic books for which the user has pre-paid, some of which are a customized selection of books related to the user's coursework and some of which are a customized selection of new best sellers. Preferably, while the user was logged-off, these customized book selections were automatically and periodically collected from third-party databases 28 by the Clearinghouse 14 based on the user's age and the Rule Module to reflect the user's interests. In this instance, the DPC 10 provides the BIA 16 with a packet containing the Universal Access Command, the Random Key Number, and any other relevant user-unique network credentials for each third party database containing the electronic books for which the user has pre-paid. The BIA 16 decrypts this package and forwards the data to the kiosk for display to the user. The displayed "Reading" icon represents the URLs of the respective third-parties' Execution Modules 38 and databases at which resides the user's customized selection of books. The kiosk forwards a Random Key Number to each of said URLs, and the respective Execution Modules 38 query the DPC 10 to authenticate the validity of each of the Random Key Numbers. For each Random Key Number validation provided by the DPC 10 to the respective URL, the user is enabled to access the respective third party database for presentation of the user's electronic books' content. In this embodiment, the user downloads the electronic books to a hand-held display panel, such as the Rocket-eBook™.

In this embodiment, the user also clicks on the "Games" icon to access an interactive Internet game site. However, as this user is actually a subordinated user on their parents' primary user accounts, the user's related Rule Modules 50 are subordinated to their parents' Internet access filtering Rule Modules 50 which restrict the user's viewing and use of Internet games when the user is not at home. In this case, the location of the BIA 16 notifies the DPC 10 that the user is attempting Internet game access from a public kiosk away from home, and the DPC 10 automatically responds with notification that user access to Internet games is denied.

Further, the user in this embodiment clicks on the "Word Processing" icon to access and edit a short story he is in the process of writing. In this instance, the BIA 16 is automatically provided by the DPC 10 with a packet containing the Universal Access Command, the Random Key Number, and any other relevant user-unique network credentials for the third party database containing the user's word processing programs and word processing content. The BIA 16 decrypts this package and forwards the data to the kiosk for display to the user. The displayed "Word Processing" icon represents the URL of the third-party Execution Module 38 and database at which resides the user's word processing software and content. The kiosk forwards a Random Key Number to said URL, and the respective Execution Module 38 queries the DPC 10 to authenticate the validity of the Random Key Number. With the DPC's validation to the URL of the Random Key Number, the user enabled to access the respective third party database for editing of the user's word processing content. It should be noted that for preferred security, this particular Random Key Number would be good for only one on-line session by the user with this third-party database.

In this embodiment, the user also clicks on the "Buddy List" icon to access their instant electronic messaging accounts. In this instance, the BIA 16 is automatically provided by the DPC 10 with a packet containing the Universal Access Command, the Random Key Number, and any other relevant user-unique network credentials for each third party database containing the instant electronic messaging accounts to which the user belongs. The BIA 16 decrypts this package and forwards the data to the kiosk for display to the user. The displayed "Buddy List" icon represents the URLs of the respective third-parties' Execution Modules 38 and databases at which reside the user's instant electronic messaging accounts. The kiosk forwards a Random Key Number to each of said URLs, and the respective Execution Modules 38 query the DPC 10 to authenticate the validity of each of the Random Key Numbers. For each Random Key Number validation provided by the DPC 10 to the respective URL, the user is enabled to access the respective third party database for instant messaging with any other on-line members of his buddy list. In this embodiment, the user's Rule Modules 50 governing the sending of instant messages by user instruct that these messages are automatically appended with both his personal visual trademark icon and digital certificate, both of which are stored in the Clearinghouse. This provides both user-customized visually graphical and cryptographically secure confirmation to recipients that the instant messages are authentically from the user.

In essence, a public kiosk without resident user-customized data and without extensive resident software, has been automatically and nearly instantly transformed, via a user's biometric log-on, into a terminal receiving on-line sophisticated computing capabilities that are customized for the user, complete with user-customized electronic transmission accessing, processing and presentation. The user has been able to personalize: their own Internet web portal displaying all URLs with which the user has pre-registered for access privileges; topical recommendations for local activities, events and people that reflect their priorities; their Internet web site preferences, or "bookmarks"; and temporary DPC 10 downloading to the BIA 16 for RAM storage of their Internet "cookies", or that set of data that an Internet website server provides to a user each time the user visits the website. In this invention, the Clearinghouse's remote servers save the information the cookie contains about the user, as a text file stored in the Netscape or Explorer system folder, and is able to temporarily download this data to whatever BIA 16 the user is currently logged onto.

In sum, the invention constructs and presents for the user, on any terminal equipped with a BIA 16 that the user may be using, a user-customized gateway to the Internet 18 containing their desired bookmarks, their personalized search engine and their customized web page directory. This is the user's personal Internet 18 web page "portal" which is a starting point for their electronic transmissions, including electronic mail, Internet 18 web browsing or "surfing", and the like.

In all of these electronic transmissions, this invention provides the user the ability, with only a single log-on, to automatically enter all restricted or confidential third-party databases 28 throughout the Internet 18 to which the user has pre-authorized access privileges.

Once the user time the user has completed their Internet 18 usage of the BIA 16 for this on-line session, all of the data stream from their on-line session, including all new cookies provided by third parties on behalf of the user and all new data on their browsing activity, is batched and forward to the DPC 10 for downloading, storage, along with any updating and revising of the user's Rule Modules 50 within the Clearinghouse. Alternatively, the user's session on-line data stream could be monitored in real-time by the DPC 10 for central server downloads and real-time revisions to the user's Rule Modules 50.

Interconnections and Communications between the Electronic Identicator and Rule Module Clearinghouse In one embodiment, the Identicator 12 module is physically distinct and separate from the Clearinghouse 14 module with each housed in independent servers or modules. In another embodiment, the Identicator is physically integrated with the Clearinghouse, whereby the Identicator 12 and Clearinghouse 14 are physically interconnected and integrated together within one server or module. In both embodiments, communications between the Identicator and the Clearinghouse 14 occur via many different methods and means that are well known in the art. Most depend on the particular communication networks already deployed by the organization or company that deploys the electronic transmission authorization system.

In one embodiment, the Identicator and the Clearinghouse 14 are connected via Ethernet to a local router, which is connected to a network operations center (NOC) via frame relay lines. Messages are sent between the Identicator and the Clearinghouse 14 using TCP/IP over this network. In another embodiment, the Identicator and the Clearinghouse 14 are connected via a cellular digital packet data (CDPD) modem to a CDPD provider, who provides TCP/IP connectivity from the Identicator to an intranet 58 to which at least one Clearinghouse 14 is attached.

In yet another embodiment, an Identicator is connected via the Internet, as is at least one Clearinghouse. TCP/IP is used to transmit messages from between the Identicator and the Clearinghouse. There are many different ways to connect the Identicator and the Clearinghouse 14 that are well understood in the industry, such as cable TV networks, cellular telephone networks, telephone networks, the Internet, an intranet, a LAN, a WAN, or an X.25 network.

The Identicator compares a user's bid biometric sample with previously stored biometric samples front registered users. After the biometric sample is stored, the user's age is then verified.

The Identicator and the Clearinghouse 14 hardware modules are high-reliability database servers, well known in the art, such as those available from Sun™, Compaq™, Tandem™, IBM™ and the like. Further, the Identicator and the Clearinghouse 14 software may incorporate scalable database architecture, well known in the art, such as those available from Oracle™, Sybase™, Informix™ and the like.

In one embodiment, once the Identicator has identified the user, to Clearinghouse accesses the Pattern Data for the user. If the user is engaged in a transaction involving age-restricted services (for example, purchasing alcohol or tobacco, or attempting to enter an age-restricted movie at a movie theater), the appropriate Pattern Data can include the user's date of birth. By comparing the user's date of birth to the current date, the Clearinghouse can determine if the user is old enough to access the service. The appropriate Execution Command can then be used to grant or deny the user access to the desired age-restricted service.

Electronic Identicator and Rule Module Clearinghouse: Master Servers and Local Servers In certain embodiments, a master Identicator is responsible for storage of the entire set of biometric samples and digital certificates registered for use with this invention. The master Clearinghouse 14 is responsible for storage of the entire set of Pattern Data 54 (including age information), Execution Commands 52, and Rule Modules 50 registered for use with this invention. The Pattern Data that includes the user's age information can be used to determine if the user is authorized to access age restricted services, such as purchasing alcohol or tobacco, or entering an age-restricted movie at a movie theater.

Each master Identicator and master Clearinghouse 14 site is preferably made up of a number of computers and databases connected together over a LAN (known in the industry). Multiple and redundant master computer sites ensure reliable service in the face of disaster or serious hardware failure at any single central computer site.

Local Identicator servers store subsets of the entire set of biometric samples, user's age information, and digital certificates registered for use with this invention. Local Clearinghouse 14 servers store subsets of the entire set of Pattern Data 54, Execution Commands 52, and Rule Modules 50 registered for use with this invention. Such Pattern Data 54 and Execution Commands 52 subsets are circumscribed by any number of criteria including, usage location, usage frequency, usage frequency, usage demographics such as age, and usage volume of electronic transmissions.

Furthermore, each master and local server site has electrical power backup and multiple redundancy in all of its critical hardware and database systems.

It is preferred that the master servers have a firewall 40 machine which is the entry point of data and messages into these computers, and a gateway machine which is a system coordinator and message processor.

Use-Sensitive Identicator and Clearinghouse Configurations

Figure 7:
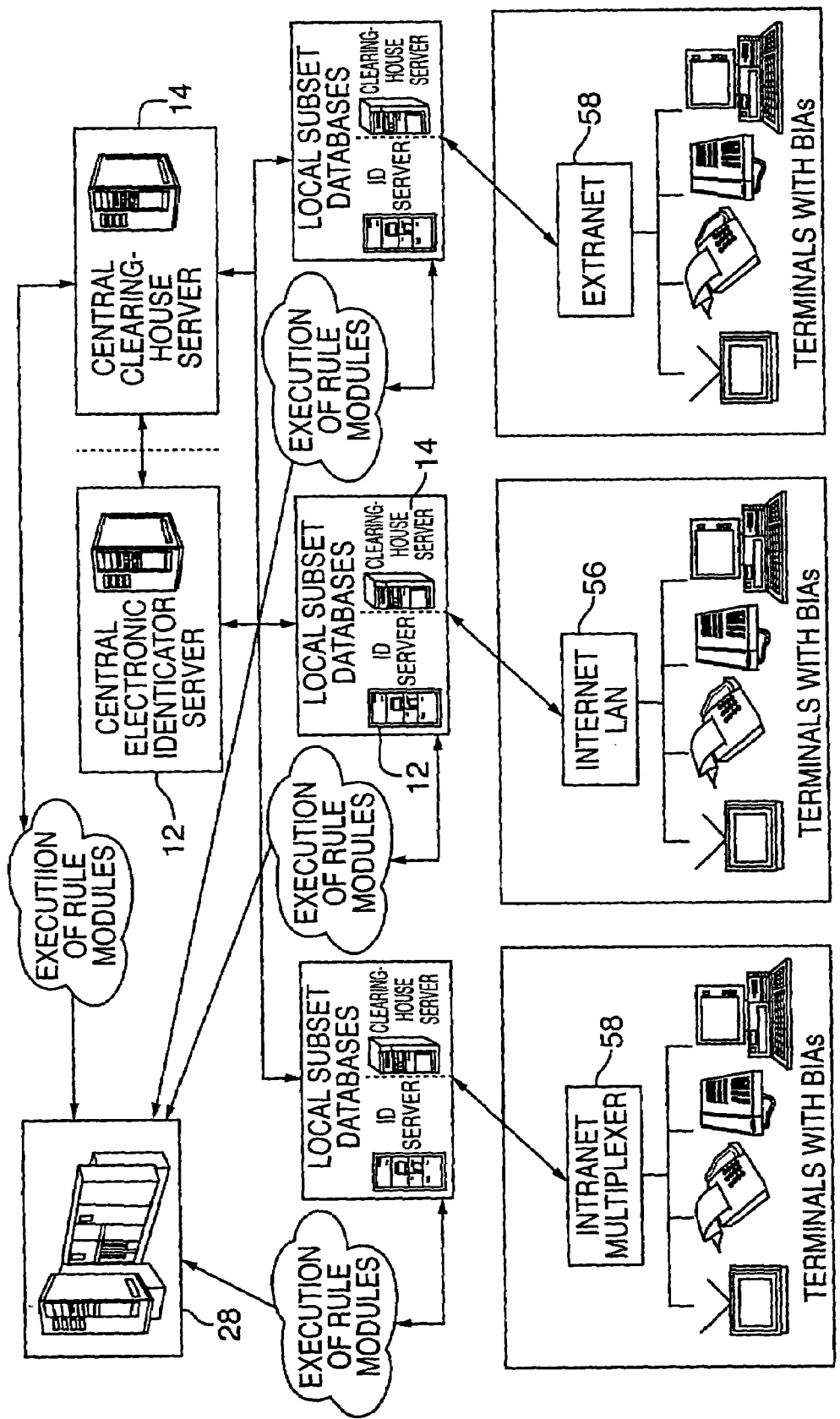
FIG. 7 shows a diagram of a user sensitive embodiment of the invention with local and central data processors.

As shown in FIG. 7, in some embodiments the invention has use-sensitive data processing capabilities, wherein multiple Identicators 12 and multiple Clearinghouses 14 exist, some of which store a subset of the total number of registered parties.

This system comprises at least one master Identicator and one master Clearinghouse, which contains a large subset of all parties registered with the system. The system further comprises at least two local Identicators or two local Clearinghouses that are physically apart from each other. Each local Identicator or Clearinghouse 14 contains a subset of the parties contained within the master Identicator or Clearinghouse. Data communications lines allow electronic transmissions to flow between each local Identicator or Clearinghouse 14 and the master Identicator or Clearinghouse.

In this embodiment, identification request electronic transmissions are first sent to the local Identicator or Clearinghouse 14 for processing. If a party cannot be identified by the local Identicator or if the requisite Rule Module is not contained in the local Clearinghouse, the electronic transmission is forwarded to the master Identicator or Clearinghouse. If the parties are identified properly by the master Identicator or if the requisite Rule Module is located in the master Clearinghouse, the electronic transmission is processed appropriately. In addition, the user's identity information and age can be transmitted from the master Identicator to the local Identicator, so that the next time the user will be successfully identified by the local Identicator.

In another embodiment of a use-sensitive system, the system further comprises a purge engine for deleting a party's user-customized information from the local Identicator and Clearinghouse 14 databases. In order to store only records for those parties who use the system more than a prescribed frequency and prevent the overload of databases with records from parties who use the system only occasionally, the record of a party is deleted from the local Identicator and Clearinghouse 14 databases if there has been no attempt to identify the party upon expiration of a predetermined time limit.

In order to make communications between the master servers and the local servers secure, the system further comprises encryption and decryption means, wherein communications between the master servers and local servers are encrypted.

Third-Party Computers

In one embodiment, an Execution Command 52 optionally requires the Clearinghouse 14 and the Execution Module 38 to communicate with at least one third-party 28 computer or database to conduct the user's command. For example, when the Execution Module 38 communicates with a host server located within an educational institution, where the third-party database 28 stores research data which is accessed in order to complete the user's Execution Command 52.

Decryption Module

In a preferred embodiment, all messages the Data Processing Center 10 receives, with the exception of those not transmitted via a BIA, contain a BIA hardware identification code, a sequence number, and a Message Authentication Code (MAC). MACs, also known as cryptographic checksums, are well known in the computer industry, and are used to assure that any changes to the content of the message will be detectable by the entity receiving the transmission. The Decryption Module 22 validates the message's MAC and checks the sequence number for that particular BIA. If the Decryption Module 22 determines that both the MAC and the sequence number are valid, the DM uses the unique secret key for that particular BIA 16 to decrypt the message. For the decryption to function properly, the Decryption Module 22 must contain a copy of each BIA's DUKPT key table.

If the decryption operation fails, or if the MAC check fails, the message is considered an invalid message. The Decryption Module 22 logs a warning to the logging facility (LF), terminates processing for the message, and returns an error message to the originating BIA.

Before the Decryption Module 22 replies to a message that includes a response key, it encrypts the response message with that response key. The Decryption Module 22 also generates a MAC for the response and appends it to the message.

Preferably, error messages are not encrypted although the Decryption Module 22 does include a MAC for message authentication. Such messages never include confidential information. However, most response messages include a status or response codes that can indicate whether the request succeeded or not. For example, when the Execution Module 38 declines a transmission for a specific reason, it does not return an error message, it returns a normal transmission response message with a response code set to "failed".

Gateway Module (GM)

The Gateway Module 26 serves as an intermediary between redundant Identicator 12 and redundant Clearinghouse 14 servers, routing electronic transmissions from servers on overload to servers that have available capacity. The Gateway Module 26 also periodically queries servers to ensure that are operative and to alert the system administrator is any server is inoperative.

Firewall (FW)

The firewall 40 provides a first line of defense against network viruses and computer hackers. All communication links into or out of the Identicator 12 and Clearinghouse 14 server sites first pass through a secure firewall 40 Machine.

Preferably, the firewall 40 Machine, an Internet local net router, only handles messages destined for the Gateway Module 26 machines.

BIA-equipped terminals send packets to Identicator 12 and Clearinghouse 14 server sites via modem, X.25, or other communication medium. The Identicator 12 and Clearinghouse 14 server sites rely on a third-party to supply the modem banks required to handle the volume of calls and feed the data onto the DPC 10 backbone.

For communications between Identicator 12 and Clearinghouse 14 server sites, the FW Machines send out double-length DES encrypted packets. The server site LAN component handles the encryption and decryption: the firewall 40 does not have the ability to decrypt the packets.

A properly configured network sniffer acts as an intruder detector as backup for the FW. If an anomalous message is detected, the intruding messages are recorded in their entirety, an operator is alerted, and the firewall 40 is physically shut down by the sniffer.

The firewall 40 disallows any transmissions from the internal network to the rest of the Internet. An electronic transmission message requires about 400 bytes and registration packets require about 10 to 20 KB. To handle 1000 electronic transmissions per second and 1 registration packet per second, the firewall 40 machines are able to process about 400 KB per second.

Execution Module

In a preferred embodiment, an Execution Command of a Rule Module 50 causes an electronic transmission to be executed by the Execution Module 38. The Execution Module 38 may be on a database which is located within the DPC 10 itself, or it may be co-located with a third-party database 28 that is external to the DPC. In the event that a designated third-party database 28 cannot be contacted for the electronic transmission to be completed, the transmission is "declined".

Logging Facility

In a preferred embodiment, the logging facility 42 logs all electronic transmission attempts, whether successful or not, to write-once media, so that a record is kept of each transmission and each error that has occurred during the operation of the Identicator.

Example Use Cases

As an example of how the present invention can be used, consider a purchaser who wants to purchase alcohol. The purchase of alcohol is restricted by law in most countries. For example, in most states in the United States, only people 21 years old or older can legally purchase alcohol. Today, verification of a purchaser's age is widely performed by having a person (e.g., a bartender, waiter/waitress, or cashier) examine a document that attests to the consumer's age: for example, a driver's license or state-issued identification card. This approach suffers from several drawbacks: first, the purchaser must obtain and carry such an identity document. Second, another person must generally examine the identity document to verify the purchaser's right to purchase alcohol, making unattended purchase problematic. Third, it is possible to tamper with or forge an identification document, allowing underage individuals to illegally gain access to alcohol.

This verification can be implemented in an improved manner using an embodiment of the present invention. This verification could be attended (e.g., at a bar, restaurant, or grocery store) or unattended (e.g., at a kiosk or vending machine).

In the case of unattended use, a kiosk of vending machine would be outfitted with a biometric input apparatus (BIA). In the case of attended use, a point of sale terminal or cash register would include or be augmented with a BIA. In either case the BIA would be as described above. The BIA would have a unique hardware identification code identifying it as a BIA being used for age verification purposes (possibly in addition to other functions).

To use the system, the purchaser would at some point register with system. This entails the purchaser providing his or her biometric and the demographic information sufficient to determine the purchaser's age. In one embodiment this demographic information would be the purchaser's age at the time of registration, while in another embodiment it would be the purchaser's date of birth. The purchaser's rule module can then associate the purchaser's age or date of birth with an Execution Command for the purchase of alcohol. This can be established manually or it can be established automatically based on the purchaser's geographic location When the purchaser is ready to purchase alcohol from the vendor, the purchaser provides a bid biometric to the system. If the system uses PICs, the purchaser can optionally provide his or her PIC as well. The bid biometric is then sent to the data processing center (DPC) where it is compared with biometrics registered with the system, as described above. If PICs are used, the offered biometric is compared with biometrics associated with the offered PIC.

Assuming a biometric match is found and the user successfully identified, the electronic identicator sends the purchaser's User ID and the hardware identification code of the BIA to the Rule Module Clearinghouse. The Rule Module Clearinghouse accesses the purchaser's rule module, and, using the purchaser's User ID and the BIA's hardware identification code, finds the Execution Command that applies to the purchase of alcohol. The purchaser's date of birth (previously registered as pattern data) is then used to determine the purchaser's age. This can be accomplished by comparing the purchaser's date of birth with a certain key date, which in the case of the purchase of alcohol would be 21 years prior to the current day. If the purchaser's date of birth is no later than the key date, then the purchaser is old enough to purchase alcohol; otherwise, the purchaser is not old enough to purchase alcohol. Alternatively, the system can compute the purchaser's age for the current day based on the purchaser's date of birth; if the purchaser exceeds the minimum legal age to purchase alcohol, the purchaser can be permitted to purchase alcohol. In another embodiment the system does not need to compute the purchaser's age because this information was already registered directly with the system. The Execution Command can be executed or not, as appropriate, which can control whether the purchaser is permitted to purchase alcohol. Execution of the Execution Command would send a positive response back to the BIA (and thus to the kiosk, vending machine, point of sale terminal, or cash register) allowing the transaction to proceed.

Because the legal age to purchase alcohol can vary based on jurisdiction, the system can use the location of the transaction (e.g., the location of the vending machine, store, etc.) as part of the data to select the appropriate Execution Command. That is, the system can apply different Execution Commands based on the purchaser's location.

The above use case describes how an Execution Command can be used to determine whether a purchaser is permitted to purchase alcohol. The foregoing discussion applies whether the purchase is occurring at a manned or unmanned position. For example, the use case could be applied to an unmanned purchase at a vending machine or other kiosk. But the use case is equally applicable to a manned purchase: for example, from a sales clerk in a store. In the case of a manned sales position, the clerk could be notified by the system that the purchaser is not eligible to purchase alcohol, and the clerk can then void the transaction. (Of course, if the purchaser could convince the clerk that the system were in error, the clerk could ignore the system's recommendation against the sale.) In addition, the while the above description focuses on the sale of alcohol, a person skilled in the art will recognize how the system can be adapted to other uses. For example, similar Execution Commands can be used to control the purchase of tobacco (e.g., cigarettes), or admission to restricted venues, such as R-rated films, having age restrictions different from those applicable to the purchase of alcohol. A person skilled in the art will also recognize how different embodiments of the invention can apply to both manned and unmanned situations.

From the foregoing, it will be appreciated how the objectives and features of the invention are met.

First, the invention provides a computerized electronic transmissions system that is tokenless. As such, this system eliminates the need for a user to possess and present any personalized man-made tokens, in order to authorize, send or receive a user-customized electronic transmission.

Second, the invention provides a computerized electronic transmissions system that is capable of verifying a user's unique personal identity including their age, as opposed to verifying the user's possession of personalized objects and information.

Third, the invention provides a cost-effective computerized electronic transmissions system that is practical, convenient, and easy use.

Fourth, the invention provides a system of secured access to a computer system that is highly resistant to fraudulent electronic transmission authorization attempts by unauthorized users and prevents users from gaining access to items that are not age-appropriate.

Fifth, the invention provides a tokenless system for ensuring that users have the portability and mobility to gain immediate access to their electronic transmissions via any network-connected interface, regardless of the resident capabilities of the computing device the user is using to interface with the computer network and a central server.

Sixth, this invention provides a user-customized "portal" or gateway to the Internet including their desired bookmarks, their personalized search engine and their customized web page directory.

Seventh, this invention provides enhanced security by maintaining authenticating data and carrying out the identity verification operations at a point in the system that is operationally isolated from the user requesting access, thereby preventing the user from acquiring copies of the authenticating data or from tampering with the verification process.

Eighth, this invention enables a user to enter and update their customized data in a centralized database.

Ninth, this invention enables primary users to both register and govern the electronic transmissions of subordinated users.

Tenth, this invention provides the ability for a third-party database to be identified by the computer system, wherein the user is notified that they have accessed the correct third-party database.

Although the invention has been described with respect to a particular computer system having rule module clearinghouse and method for its use, it will be appreciated that various modifications of the apparatus and method are possible without departing from the invention, which is defined by the claims set forth below.

What is claimed is:

1. A method implemented in a computer system including at least one computer for providing approval of an age-restricted transaction conducted by an age presenter, comprising:

receiving, at an unattended age verification station, at least one biometric sample proffered by the age presenter via a biometric identification device coupled to the computer system;

sending the at least one biometric sample to at least one database in the computer system, wherein the at least one database has at least one biometric record stored therein, wherein the at least one biometric record contains a reference of the age presenter's age;

comparing, at the at least one database, the at least one biometric sample to the at least one biometric record stored in the at least one database;

making a first determination, at the at least one database, whether the at least one biometric sample matches the at least one biometric record stored in the at least one database;

in the event the at least one biometric sample matches the at least one biometric record stored in the at least one database, making a second determination whether the age presenter's age information in the reference meets at least one system parameter;

in the event that the age presenter's age mapped to the biometric record meets the at least one system parameter, approving the age-restricted transaction at the at least one database; and receiving, at the unattended age verification station, confirmation of the age-restricted transaction approval.

2. The method of claim 1, wherein the at least one system parameter is defined by the age verification station.

3. The method of claim 1, wherein the at least one biometric sample comprises at least one of a fingerprint scan, an iris scan, a facial scan, a voice scan, a retinal scan, a hand architecture scan, a vein pattern scan, a signature sample, and a DNA sample.

4. The method of claim 1, wherein the at least one biometric record comprises at least one digital representation of a fingerprint scan, an iris scan, a facial scan, a voice scan, a retinal scan, a hand architecture scan, a vein pattern scan, a signature sample, and a DNA sample.

5. The method of claim 1, wherein the steps of sending and receiving comprise sending and receiving encrypted data.

6. The method of claim 1, wherein sending the at least one biometric sample to the at least one database further comprising sending at least one of a location for the unattended age verification station, a time of age-restricted transaction, a transaction type, a reference code, a detailed access record, and blood alcohol content of the age presenter.

7. The method of claim 1, wherein a system users s information is stored in the at least one database.

8. The method of claim 7, wherein transaction information pertaining to the age-restricted transaction is compared to the system user information stored in the at least one database.

9. The method of claim 1, wherein the unattended age verification station is selected from the group consisting of a vending machine, a kiosk, a PC, a wireless device, a computing device, and a storage device.

10. The method of claim 1, wherein the unattended age verification station is an unattended point of sale device.

11. The method of claim 10, wherein the age-restricted transaction comprises a financial transaction.

12. The method of claim 11, wherein the financial transaction settlement is conducted via a financial transaction system, wherein the financial transaction system comprises the at least one biometric sample being used to authenticate the financial transaction settlement.

13. The method of claim 1, wherein the second determination comprises a reliability determination and includes assessing whether or not the at least one biometric sample is being used fraudulently.

14. A method implemented in a computer system including at least one computer for providing approval of an age-restricted transaction conducted by an age presenter, comprising:

receiving, at an unattended age verification station, at least one biometric sample proffered by the age presenter via a biometric identification device coupled to the computer system;

receiving, at the unattended age verification station, at least one identification code proffered by the age presenter;

sending the identification code proffered by the age presenter from the unattended age verification station to at least one database in the computer system;

wherein the at least one database has at least one biometric record stored therein, wherein the at least one biometric record contains a reference of the age presenter's age, and wherein the at least one database has at least one identification code record;

comparing, at the at least one database, the at least one identification code proffered by the age presenter to the at least one identification code record;

making, at the at least one database, a first determination whether the at least one identification code proffered by the age presenter matches at least identification code record;

in the event the at least one identification code matches the at least one identification code record, making a second determination whether the reference meets at least one system parameter;

in the event the reference meets the at least one system parameter, pre-approving, at the at least one database, the at least one biometric record as a potential matching biometric record;

receiving, at the unattended age verification station, the potential matching biometric record from the at least one database;

comparing, at the unattended age verification station, the at least one biometric sample with the potential matching biometric record;

making, at the unattended age verification station, a third determination whether the at least one biometric sample matches the potential matching biometric record;

in the event that the at least one biometric sample matches the potential matching biometric record;

making, at the unattended age verification station, a fourth determination whether the matching biometric record was pre-approved at the at least one database; and in the event the matching biometric record was pre-approved at the at least one database, approving, at the unattended age verification station, the age-restricted transaction.

15. The method of claim 14, wherein the at least one system parameter is defined by the age verification station.

16. The method of claim 14, further comprising the age verification station sending to the at least one database confirmation of completion of the age-restricted transaction.

17. The method of claim 14, wherein the at least one biometric sample comprises at least one of a fingerprint scan, an iris scan, a facial scan, a voice scan, a retinal scan, a hand architecture scan, a vein pattern scan, a signature sample, and a DNA sample.

18. The method of claim 14, wherein the at least one biometric record comprises at least one digital representation of a fingerprint scan, an iris scan, a facial scan, a voice scan, a retinal scan, a hand architecture scan, a vein pattern scan, a signature sample, and a DNA sample.

19. The method of claim 14, wherein the at least one identification code, comprises at least one of a unique number, a reasonably unique number, and a non unique number.

20. The method of claim 14, wherein the steps of sending and receiving comprise sending and receiving encrypted data.

21. The method of claim 14, wherein sending the at least one biometric sample to the at least one database further comprising sending at least one of a location for the age unattended age verification station, a time of age-restricted transaction, a transaction type, a reference code, a detailed access record, and blood alcohol content of the age presenter.

22. The method of claim 14, wherein a system user information is stored in the at least one database.

23. The method of claim 22, wherein a transaction information pertaining to the age-restricted transaction is compared to the system user information stored in the at least one database.

24. The method of claim 14, wherein the unattended age verification station is selected from the group consisting of a vending machine, a kiosk, a PC, a wireless device, a computing device, and a storage device.

25. The method of claim 14, wherein the unattended age verification station is an unattended point of sale device.

26. The method of claim 25, wherein the age-restricted transaction comprises a financial transaction.

27. The method of claim 26, wherein the financial transaction settlement is conducted via a financial transaction system, wherein the financial transaction system comprises the at least one biometric sample being used to authenticate the financial transaction settlement.

28. The method of claim 14, further comprising prompting the age presenter for an additional transaction once the age-restricted transaction is completed.

29. The method of claim 14, wherein the second determination comprises a reliability determination and includes assessing whether or not the at least one biometric sample is being used fraudulently.

30. A method implemented in a computer system including at least one computer for providing approval of an age-restricted transaction conducted by an age presenter, comprising:
    receiving, at an unattended age verification station, at least one biometric sample proffered by the age presenter via a biometric identification device coupled to the computer system;
    receiving, at the unattended age verification station, at least one age-restricted action proposal proffered by the age presenter;
    associating at least one proposal code with the at least one age-restricted action proposal;
    sending an identification code proffered by the age presenter from the unattended age verification station to at least one database in the computer system;
    wherein the at least one database has at least one biometric record stored therein, wherein the at least one biometric record contains a reference of the age presenter's age, and wherein the at least one database has at least one identification code record;
    sending the at least one proposal code affiliated with the age-restricted action proposal proffered by the age presenter from the unattended age verification station to the database;
    comparing, at the at least one database, the at least one biometric sample to the at least one biometric record;
    making a first determination, at the at least one database, whether the biometric sample matches the at least one biometric record;
    in the event the at least one biometric sample matches the at least one biometric record, making a second determination whether the reference meets a parameter, wherein the parameter is indicated by the at least one proposal code;
    in the event the reference meets the parameter, approving the age-restricted transaction at the at least one database; and
    receiving, at the unattended age verification station, confirmation of the age-restricted transaction approval.

31. The method of claim 30, wherein the age presenter proffers a plurality of the at least one age-restricted action proposals, wherein the plurality of age-restricted action proposals contain a plurality of age restrictions 32. The method of claim 30, wherein the at least one biometric sample comprises at least one of a fingerprint scan, an iris scan, a facial scan, a voice scan, a retinal scan, a hand architecture scan, a vein pattern scan, a signature sample, and a DNA sample.

33. The method of claim 30, wherein the at least one biometric record comprises at least one digital representation of a fingerprint scan, an iris scan, a facial scan, a voice scan, a retinal scan, a hand architecture scan, a vein pattern scan, a signature sample, and a DNA sample.

34. The method of claim 30, wherein the steps of sending and receiving comprise sending and receiving encrypted data.

35. The method of claim 30, wherein sending the at least one biometric sample to the at least one database further comprising sending at least one of a location for the age unattended age verification station, a time of age-restricted transaction, a transaction type, a reference code, a detailed access record, and blood alcohol content of the age presenter.

36. The method of claim 30, wherein a system user information is stored in the at least one database.

37. The method of claim 36, wherein a transaction information pertaining to the age-restricted transaction is compared to the system user information stored in the at least one database.

38. The method of claim 30, wherein the unattended age verification station is selected from the group consisting of a vending machine, a kiosk, a PC, a wireless device, a computing device, and a storage device.

39. The method of claim 30, wherein the unattended age verification station is an unattended point of sale device.

40. The method of claim 39, wherein the age-restricted transaction comprises a financial transaction.

41. The method of claim 40, wherein the financial transaction settlement is conducted via a financial transaction system, wherein the financial transaction system comprises the at least one biometric sample being used to authenticate the financial transaction settlement.

42. The method of claim 30, further comprising prompting the age presenter for an additional transaction once the age-restricted transaction is completed.

43. The method of claim 30, wherein the second determination comprises a reliability determination reliability determination includes assessing whether or not the at least one biometric sample is being used fraudulently.

44. A method implemented in a computer system including at least one computer for providing approval of an age-restricted transaction conducted by an age presenter, comprising:
    receiving, at an unattended age verification station, at least one biometric sample proffered by the age presenter via a biometric identification device coupled to the computer system;

receiving, at the unattended age verification station, at least one identification code proffered by the age presenter in the computer system;

receiving, at the unattended age verification station, at least one age-restricted action proposal proffered by the age presenter;

sending the identification code proffered by the age presenter from the unattended age verification station to at least one database;

wherein the at least one database has at least one biometric record stored therein, wherein the at least one biometric record contains a reference of the age presenter's age, and wherein the at least one database has at least one identification code record;

associating at least one proposal code with the at least one age-restricted action proposal;

sending the at least one proposal code to the at least one database;

comparing, at the at least one database, the at least one identification code to the at least one identification code record;

making, at the database, a first determination whether the at least one identification code matches the at least one age presenter identification code;

in the event the at least one age presenter identification code matches the at least one age presenter identification code, making a second determination whether the reference meets at least one system parameter, wherein the at least one parameter is indicated by the at lest one proposal code;

in the at least one parameter is met, pre-approving, at the at least one database, the at least one biometric record as a potential matching biometric record for age verification approval at the age verification station;

receiving, at the unattended age verification station, the potential matching biometric record;

comparing, at the unattended age verification station, the at least one biometric sample to the potential matching biometric record;

making, at the unattended age verification station, a third determination of whether the at least one biometric sample matches the potential matching biometric record;

in the event that the at least one biometric sample matches the potential matching biometric record;

making, at the unattended age verification station, a fourth determination whether the matching biometric record was pre-approved at the at least one database; and in the event the at least one biometric record was pre-approved at the at least one database, approving, at the unattended verification station, the age-restricted transaction.

45. The method of claim 44, wherein the age presenter proffers a plurality of the at least one age-restricted action proposals, wherein the plurality of age-restricted action proposals contain a plurality of age restrictions.

46. The method of claim 44, further comprising the age verification station sending to the at least one database confirmation of completion of the age-related transaction.

47. The method of claim 44, wherein the at least one biometric sample comprises at least one of a fingerprint scan, an iris scan, a facial scan, a voice scan, a retinal scan, a hand architecture scan, a vein pattern scan, a signature sample, and a DNA sample.

48. The method of claim 44, wherein the at least one biometric record comprises at least one digital representation of a fingerprint scan, an iris scan, a facial scan, a voice scan, a retinal scan, a hand architecture scan, a vein pattern scan, a signature sample, and a DNA sample.

49. The method of claim 44, wherein the steps of sending and receiving comprise sending and receiving encrypted data.

50. The method of claim 44, wherein sending the at least one biometric sample to the at least one database further comprising sending at least one of a location for the age unattended age verification station, a time of age-restricted transaction, a transaction type, a reference code, a detailed access record, and blood alcohol content of the age presenter.

51. The method of claim 44, wherein a system user information is stored in the at least one database.

52. The method of claim 51, wherein a transaction information pertaining to the age-restricted transaction is compared to the system user information stored in the at least one database.

53. The method of claim 44, wherein the unattended age verification station is selected from the group consisting of a vending machine, a kiosk, a PC, a wireless device, a computing device, and a storage device.

54. The method of claim 44, wherein the unattended age verification station is an unattended point of sale device.

55. The method of claim 54, wherein the age-restricted transaction comprises a financial transaction.

56. The method of claim 55, wherein the financial transaction settlement is conducted via a financial transaction system, wherein the financial transaction system comprises the at least one biometric sample being used to authenticate the financial transaction settlement.

57. The method of claim 44, wherein an unattended age verification station offers the age presenter an additional access in conjunction with the age-restricted transaction.

58. The method of claim 44, wherein the second determination comprises a reliability determination and includes assessing whether or not the at least one biometric sample is being used fraudulently.

59. A method implemented in a computer system including at least one computer for providing approval of an age-restricted transaction conducted by an age presenter, comprising:

receiving, at an unattended age verification station, at least one biometric sample proffered by the age presenter via a biometric identification device coupled to the computer system;

receiving, at the unattended age verification station, at least one identification code proffered by the age presenter;

sending the identification code proffered by the age presenter from the unattended age verification station to at least one database in the computer system;

wherein the at least one database has at least one biometric record stored therein, wherein the at least one biometric record contains a reference of the age presenter's age, and wherein the at least one database has at least one identification code record;

comparing, at the at least one database, the at least one identification code to the at least one identification code record;

making, at the at least one database, a first determination whether the at least one identification code matches at least identification code record;

in the event the at least one identification code matches the at least one identification code record, sending at least one biometric record to at the unattended age verification station;

receiving, at the unattended age verification station, the at least one biometric record with the reference;

comparing, at the unattended age verification station, the at least one biometric sample to the at least one biometric record;

making, at the unattended age verification station, a second determination of whether the at least one biometric sample matches the at least one biometric record;

in the event that the at least one biometric sample matches the at least one biometric record, making, at the unattended age verification station, a third determination of an access level that is associated with the reference; and approving, at the unattended age verification station, an age-verification access level for the transaction.

60. The method of claim 59, further comprising the age verification station sending to the at least one database confirmation of completion of the age-related transaction.

61. The method of claim 59, wherein the at least one biometric sample comprises at least one of a fingerprint scan, an iris scan, a facial scan, a voice scan, a retinal scan, a hand architecture scan, a vein pattern scan, a signature sample, and a DNA sample.

62. The method of claim 59, wherein the at least one biometric record comprises at least one digital representation of a fingerprint scan, an iris scan, a facial scan, a voice scan, a retinal scan, a hand architecture scan, a vein pattern scan, a signature sample, and a DNA sample.

63. The method of claim 59, wherein the steps of sending and receiving comprise sending and receiving encrypted data.

64. The method of claim 59, wherein sending the at least one biometric sample to the at least one database further comprising sending at least one of a location for the age unattended age verification station, a time of age-restricted transaction, a transaction type, a reference code, a detailed access record, and blood alcohol content of the age presenter.

65. The method of claim 59, wherein a system user information is stored the at least one database.

66. The method of claim 65, wherein a transaction information pertaining to the age-restricted transaction is compared to the system user information stored in the at least one database.

67. The method of claim 66, wherein the unattended age verification station is selected from the group consisting of a vending machine, a kiosk, a PC, a wireless device, a computing device, and a storage device.

68. The method of claim 59, wherein the unattended age verification station is an unattended point of sale device.

69. The method of claim 68, wherein the age restricted transaction comprises a financial transaction.

70. The method of claim 69, wherein the financial transaction settlement is conducted via a financial transaction system, wherein the financial transaction system comprises the at least one biometric sample being used to authenticate the financial transaction settlement.

71. The method of claim 59, further comprising prompting the age presenter for an additional transaction once the age-restricted transaction is completed.

72. The method of claim 59, wherein the second determination comprises a reliability determination and includes assessing whether or not the at least one biometric sample is being used fraudulently.

73. A method implemented in a computer system including at least one computer for enrolling a system user in a transaction system comprising:

providing at least one unattended age verification station coupled to the computer system, wherein the least one unattended age verification station is configured to access at least one database in the computer system, wherein the at least one database has at least one biometric record stored therein, wherein the at least one biometric record is associated with the system user and contains a reference of the age presenter's age;

prompting the system user to proffer an enrollment data comprising age information, personal information, and at least one biometric sample;

transmitting to the at least one database the enrollment data; and storing in the at least one database the enrollment data.

74. The method of claim 73, wherein the reference is a record of at least one of a government issued identification data, a driver's license data, a passport data, a birth certificate data, and a credit data.

75. The method of claim 73, wherein the enrollment data comprises at least one of a driver's license data, a social security number, an address, and a phone number.

76. The method of claim 73, wherein the enrollment data is acquired via a process selected from the group consisting of swiping, scanning and hand-keying.

77. The method of claim 73, wherein the at least one biometric sample is entered via a biometric scanner.

78. The method of claim 73, where in the at least one unattended age verification station is selected from the group consisting of a verifier station, a merchant's store, a government office, a bank, a kiosk, a vending machine, a personal computer and a wireless device.

79. The method of claim 73, wherein the system user additionally proffers an age presenter identification code.

80. The method of claim 79, wherein the age presenter identification code comprises at least one of a unique number and a reasonably unique number.

81. The method of claim 73, wherein the at least one biometric sample comprises at least one of a fingerprint scan, an iris scan, a facial scan, a voice scan, a retinal scan, and a hand architecture scan.

82. The method of claim 73, wherein the step of storing the enrollment data in the at least one database comprises: converting the at least one biometric sample into a biometric template; and saving the biometric template to the at least one database.

83. The method of claim 73, where in the enrollment data comprises a digital image of the at least one biometric sample.

84. The method of claim 73, wherein the enrollment data comprises a record maintenance password.

85. The method of claim 84, wherein the record maintenance password allows the system user to access and change the biometric record.

86. The method of claim 73, wherein the enrollment data comprises a digital image of at least one document presented for at least one of a system user identification and a system user age verification.

87. The method of claim 73, wherein the proffered enrollment data comprises financial account information.

88. The method of claim 12, further comprising prompting the age presenter to add an additional purchase selection to the transaction.

89. The method of claim 1, further comprising prompting the age presenter to add an additional age-restricted selection to the transaction.

90. The method of claim 73, wherein the method further comprises a system operator verifies the enrollment data.

91. The method of claim 90, wherein the system operator is remote from the system user.

92. The method of claim 90, wherein verification of the enrollment data is sent to the at least one database and stored in the at least one biometric record.

93. The method of claim 90, wherein verification comprises at least one of proffering a biometric scan, proffering an identification code, and pressing a designated key.

94. A method implemented in a computer system including at least one computer for pre-enrolling a system user in a transaction system comprising:
providing at least one unattended age verification station coupled to the computer system, wherein the at least one unattended age verification station is configured to access at least one database in the computer system, wherein the at least one database stores at least one biometric record, wherein the at least one biometric record is associated with the system user and wherein the biometric record has the capacity to contain a reference of the age of the system user:
prompting a system user to proffer an enrollment data, wherein the enrollment data is less than an amount of data needed for a complete enrollment;
transmitting to the at least one database the enrollment data; and
storing in the at least one database the enrollment data.

95. The method of claim 94, wherein the enrollment data comprises at least one of age verifying information, identity verifying information, and biometric information.

96. The method of claim 94, further comprising finalizing enrollment, wherein the system user proffers additional information not proffered during pre-enrollment, wherein the additional information is selected from the group consisting of age verifying information, identity verifying information, and biometric information.

97. The method of claim 96, wherein the enrollment data is verified by a system operator.

98. The method of claim 97, wherein verification of the enrollment data comprises at least one of proffering a biometric scan, proffering an identification code, and pressing a designated key.

99. A method implemented in a computer system including at least one computer for pre-enrolling a system user in a transaction system comprising:
providing at least one unattended age verification station coupled to the computer system, wherein the at least one unattended age verification station is configured to access at least one database in the computer system, wherein the at least one database stores at least one biometric record, wherein the at least one biometric record is associated with the system user and wherein the biometric record has the capacity to contain a reference of the age of the system user:
prompting a database operator to proffer for the system user an enrollment data, wherein the enrollment data is less than an amount of data need for a complete enrollment;
transmitting to the at least one database the enrollment data; and
storing in the at least one database the enrollment data.

100. The method of claim 99, wherein the enrollment data comprises at least one of age verifying information, identity verifying information, and biometric information.

101. The method of claim 99, further comprising finalizing enrollment, wherein the system user proffers additional information not proffered during pre-enrollment, wherein the additional information is selected from the group consisting of age verifying information, identity verifying information, and biometric information.

102. The method of claim 101, wherein the enrollment data is verified by at least one of a system operator and database operator.

103. The method of claim 102, wherein verification of the enrolment data comprises at least one of proffering a biometric scan, proffering an identification code, and pressing a designated key.

* * * * *